(12) United States Patent
Plath et al.

(10) Patent No.: US 7,851,411 B2
(45) Date of Patent: *Dec. 14, 2010

(54) α-CYANOACRYLATES

(75) Inventors: Peter Plath, Frankenthal (DE); Norbert Götz, Worms (DE); Michael Rack, Heidelberg (DE); Andreas Landes, Römerberg-Heiligenstein (DE); Cyrill Zagar, Mannheim (DE); Matthias Witschel, Bad Dürkheim (DE); Klaus Großmann, Neuhofen (DE)

(73) Assignee: BASF SE, Ludwigshafen (DE)

( * ) Notice: Subject to any disclaimer, the term of this patent is extended or adjusted under 35 U.S.C. 154(b) by 1782 days.

This patent is subject to a terminal disclaimer.

(21) Appl. No.: 10/499,522

(22) PCT Filed: Dec. 17, 2002

(86) PCT No.: PCT/EP02/14353

§ 371 (c)(1),
(2), (4) Date: Jun. 21, 2004

(87) PCT Pub. No.: WO03/051824

PCT Pub. Date: Jun. 26, 2003

(65) Prior Publication Data

US 2005/0009706 A1    Jan. 13, 2005

(51) Int. Cl.
A01N 43/36     (2006.01)
A01N 37/00     (2006.01)
A01N 37/34     (2006.01)
C07D 295/104   (2006.01)
C07D 305/06    (2006.01)
C07C 255/07    (2006.01)

(52) U.S. Cl. .................. 504/287; 504/307; 504/312; 548/540; 549/510; 558/438; 558/443; 558/445

(58) Field of Classification Search .................. None
See application file for complete search history.

(56) References Cited

U.S. PATENT DOCUMENTS

| 4,201,569 A |   | 5/1980 | Hedrich |         |
|-------------|---|--------|---------|---------|
| 4,902,334 A | * | 2/1990 | Azuma et al. | 504/176 |
| 4,935,052 A |   | 6/1990 | Huppatz et al. |     |
| 5,198,014 A | * | 3/1993 | Maravetz | 504/225 |

FOREIGN PATENT DOCUMENTS

| DE | 100 21 900 | 11/2001 |
| EP | 0 104 432  | 4/1984  |
| JP | 59/051202  | 3/1984  |
| JP | 60/078902  | 5/1985  |

OTHER PUBLICATIONS

Hayashi, et al. (AN 1968:82967 ZCAPLUS, abstract of Bulletin of Chemical SOciety of Japan (1967), 40(9), 2160-3).*
GLickman et al. (AN 1945:20676, ZCAPLUS, abstract of J. of Am. Chem Soc. (1945), 67, 1012-16).*
Campbell et al. (AN 1911:8811, ZCAPLUS, abstract of Proc. Chem. Soc. (1911), 26, 2296).*
Campbell et al. (AN 1911:8812, ZCAPLUS, abstract of J. of the Chem. Soc. Transcation (1910), 97, 2418-25).*
Hayashi et al., Bulletin of the Chemical Society of Japan, vol. 40, pp. 2160-2163 (1967).*
Hiramatsu et al., "Herbicide" English Abstract of document (AB).
Hiramatsu et al., "Herbicide, Weed Killing Method and Plant-Growth Regulator" English Abstract of document (AC).
McFadden et al., "X-Ray Structure Analysis of a Cyanoacrylate Inhibitor of Photosystem II Electron Transport" Zeitschrift für Naturforschung C, Journal of Biosciences 46(1-2), 93-98 (1991).
Bulletin of the Chemical Society of Japan, vol. 40, 2160-2163 (1967)_Hayashi et al., Studies on Geometric Isomerism by Nuclear Magnetic Resonance. IV.
JP 61109752 = Abstract, original document published May 28, 1986.

* cited by examiner

*Primary Examiner*—Kamal A Saeed
*Assistant Examiner*—Alicia L Otton
(74) *Attorney, Agent, or Firm*—Novak Druce + Quigg LLP

(57) ABSTRACT

α-Cyanoacrylates of the formula I, where: $R^1$ is $OR^a$ wherein $R^a$ is hydrogen, substituted alkyl, branched alkyl, branched alkenyl, cycloloalkyl, heterocyclyl, aryl, phenylalkyl or alkylimino; is $NR^bR^c$ wherein $R^b$ is hydrogen, alkyl which may be substituted, alkenyl, alkynyl; $R^c$ is hydrogen, alkyl which may be substituted alkenyl, alkynyl, cycloalkyl, heterocyclyl, aryl, phenylalkyl or alkylimino; or $R^b$ and $R^c$ form an alkandiyl-chain which may be substituted; or is $SR^d$ wherein $R^d$ is hydrogen, alkyl which may be substituted, alkenyl, alkynyl, cycloalkyl, heterocyclyl, aryl, phenylalkyl or alkylimino; $R^2$ is alkyl which may be substituted; is alkenyl or alkynyl; $R^3$ is alkyl may be substituted; is alkenyl or alkynyl; $R^4$ is hydrogen, halogen, cyano or alkyl; and their agriculturally useful salts, processes and intermediates for their preparation; and the use of these compounds or of compositions comprising these compounds for controlling undesirable plants are described.

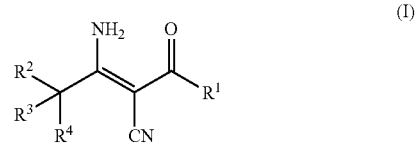

(I)

15 Claims, No Drawings

α-CYANOACRYLATES

The present invention relates to α-cyanoacrylates of the formula I

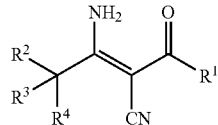

where:
- $R^1$ is $OR^a$ wherein $R^a$ is hydrogen, $C_1$-$C_6$-alkyl which is partially or fully halogenated and/or carries a substituent from the group consisting of hydroxy, cyano, $C_3$-$C_6$-cycloalkyl, three- to six-membered heterocyclyl, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, ($C_1$-$C_4$)alkoxycarbonyl, aminocarbonyl, ($C_1$-$C_6$)alkylaminocarbonyl, di($C_1$-$C_6$)alkylaminocarbonyl;
  is branched $C_3$-$C_6$-alkyl, branched $C_4$-$C_6$-alkenyl, $C_3$-$C_6$-alkynyl, $C_3$-$C_6$-cycloalkyl, four- to six-membered heterocyclyl, aryl, phenyl($C_1$-$C_4$)alkyl or ($C_1$-$C_6$)alkylimino;
  is $NR^bR^c$ wherein $R^b$ is hydrogen, $C_1$-$C_6$-alkyl which may be partially or fully halogenated and/or may carry a substituent from the group consisting of hydroxy, cyano, $C_1$-$C_6$-alkoxy, $C_1$-$C_6$-haloalkoxy, $C_1$-$C_6$-alkylthio, $C_1$-$C_6$-halogenalkylthio, $C_1$-$C_6$-alkylsulfinyl, $C_1$-$C_6$-halogenalkylsulfinyl, $C_1$-$C_6$-alkylsulfonyl and $C_1$-$C_6$-halogenalkylsulfonyl;
  is $C_2$-$C_6$-alkenyl, $C_2$-$C_6$-alkynyl;
  $R^c$ is hydrogen, $C_1$-$C_6$-alkyl which may be partially or fully halogenated and/or may carry a substituent from the group consisting of hydroxy, cyano, $C_3$-$C_6$-cycloalkyl, three- to six-membered heterocyclyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, ($C_1$-$C_4$)alkoxycarbonyl, aminocarbonyl, ($C_1$-$C_6$)alkylaminocarbonyl, di ($C_1$-$C_6$)alkylaminocarbonyl;
  is $C_3$-$C_6$-alkenyl, $C_3$-$C_6$-alkynyl, $C_3$-$C_6$-cycloalkyl, four-to-six-membered heterocyclyl, aryl, phenyl($C_1$-$C_4$-)alkyl or ($C_1$-$C_6$)alkylimino;
  or $R^b$ and $R^c$ together from a 1,4-butanediyl-, 1,5-pentanediyl- or 1,6-hexanediyl—chain, wherein each of the chains may carry one or more $C_1$-$C_6$-alkyl-groups; or
  is $SR^d$ wherein $R^d$ has the some meaning as $R^c$;
- $R^2$ is $C_1$-$C_6$-alkyl which may be partially or fully halogenated and/or may carry a substituent from the group consisting of cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl;
  is $C_2$-$C_6$-alkenyl or $C_2$-$C_6$-alkynyl;
- $R^3$ is $C_2$-$C_6$-alkyl or $C_1$-$C_6$-alkyl which is partially or fully halogenated and/or carries a substituent from the group consisting of cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl;
  is $C_2$-$C_6$-alkenyl or $C_2$-$C_6$-alkynyl;
- $R^4$ is hydrogen, halogen, cyano or $C_1$-$C_6$-alkyl, and their agriculturally useful salts.

Moreover, the invention relates to processes and intermediates for preparing compounds of formula I, to compositions comprising them and to the use of these derivatives or the compositions comprising them for controlling harmful plants.

α-Cyano-β-aminoalkylacrylic esters are known from the literature, for example from Hayashi et al., Bull. Chem. Soc. Jpn. 40, (1967), 2160-2163. JP 61109752 discloses α,β-unsaturated carboxylic acid derivatives as plant growth regulators. WO 98/00598 (=U.S. Pat. No. 4,902,334) discloses herbicidally active crotonic acid derivatives.

However, the herbicidal properties of the prior-art compounds and/or their compatibility with crop plants are not entirely satisfactory. It is therefore an object of the present invention to provide novel, in particular herbicidally active, compounds having improved properties.

We have found that this object is achieved by the α-cyanoacrylates of formula I and their herbicidal activity.

Furthermore, we have found herbicidal compositions which comprise the compounds I and have very good herbicidal activity. Moreover, we have found processes for preparing these compositions and methods for controlling undesirable vegetation using the compounds I.

The α-cyanoacrylates of formula I are always present as (Z) isomers, i.e. amino group and ester radical are on the same side of the double bond.

Depending on the substitution pattern, the compounds of formula I can contain one or more chiral centers, in which case they are present as enantiomers or mixtures of diastereomers. This invention provides both the pure enantiomers or diastereomers and mixtures thereof.

The compounds of formula I can also be present in the form of their agriculturally useful salts, where the type of salt is usually immaterial. In general, suitable salts are the salts of those cations or the acid addition salts of those acids whose cations and anions, respectively, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where here, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di-(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri ($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate, and also the anions of $C_1$-$C_4$-alkanoic acids, preferably formate, acetate, propionate and butyrate.

The organic moieties mentioned for the substituents $R^1$-$R^7$ and $R^a$-$R^d$ are collective terms for individual enumerations of the individual group members. All hydrocarbon chains, i.e. all alkyl, alkenyl, alkynyl, haloalkyl, cyanoalkyl, alkoxy, haloalkoxy, alkylthio, haloalkylthio, alkylsulfinyl, haloalkylsulfinyl, alkylsulfonyl and haloalkylsulfonyl moieties can be straight-chain or branched unless indicated otherwise. Unless indicated otherwise, halogenated substituents preferably carry one to five identical or different halogen atoms. The term halogen represents in each case fluorine, chlorine, bromine or iodine.

Examples of other meanings are:

$C_1$-$C_4$-alkyl as well as the alkyl parts of ($C_1$-$C_4$)-alkoxycarbonyl and phenyl($C_1$-$C_4$)alkyl: for example methyl, ethyl, propyl, 1-methylethyl, butyl, 1-methylpropyl, 2-methylpropyl and 1,1-dimethylethyl;

$C_1$-$C_6$-alkyl as well as the alkyl parts of ($C_1$-$C_6$)alkyl aminocarbonyl, di($C_1$-$C_6$)alkylaminocarbonyl and $C_1$-$C_6$-alkylimino: $C_1$-$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

branched $C_3$-$C_6$-alkyl: a branched saturated hydrocarbon having 3 to 6 carbon atoms, such as, for example, 1-methylethyl, 1-methylpropyl, 2-methylpropyl, 1,1-dimethylethyl, 1-methylbutyl, 2-methylbutyl, 3-methylbutyl, 2,2-dimethylpropyl, 1-ethylpropyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_3$-$C_6$-cycloalkyl: a monocyclic saturated hydrocarbon having 3 to 6 ring members, such as cyclopropyl, cyclobutyl, cyclopentyl and cyclohexyl, four- to six-membered heterocyclyl: a monocyclic, saturated or partial unsaturated cycle having four to six ring members, which comprises apart from carbon atoms one to four nitrogen atoms, or one or two oxygen atoms, or one or two sulfur atom, or one to three nitrogen atoms and an oxygen atom, or one to three nitrogen atoms and a sulfur atom, or one sulfur and one oxygen atom, for example:

three- or four-membered heterocycles like 2-oxetanyl, 3-oxetanyl, 2-thiethanyl, 3-thiethanyl, 1-azetidinyl, 2-azetidinyl, 1-azetinyl, 2-azetinyl;

five membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl;

five membered partial unsaturated heterocycles like 2,3-dihydrofur-2-yl, 2,3-dihydrofur-3-yl, 2,4-dihydrofur-2-yl, 2,4-dihydrofur-3-yl, dioxolan-2-yl, 1,3-dioxol-2-yl, 2,3-dihydrothien-2-yl, 2,3-dihydrothien-3-yl, 2,4-dihydrothien-2-yl, 2,4-dihydrothien-3-yl, 4,5-dihydropyrrol-1-yl, 4,5-dihydropyrrol-2-yl, 4,5-dihydropyrrol-3-yl, 2,5-dihydropyrrol-1-yl, 2,5-dihydropyrrol-2-yl, 2,5-dihydropyrrol-3-yl, 2,3-dihydroisoxazol-1-yl, 2,3-dihydroisoxazol-3-yl, 2,3-dihydroisoxazol-4-yl, 2,3-dihydroisoxazol-5-yl, 2,5-dihydroisoxazol-3-yl, 2,5-dihydroisoxazol-4-yl, 2,5-dihydroisoxazol-5-yl, 4,5-dihydroisoxazol-2-yl, 4,5-dihydroisoxazol-3-yl, 4,5-dihydroisoxazol-4-yl, 4,5-dihydroisoxazol-5-yl, 2,3-dihydroisothiazol-1-yl, 2,3-dihydroisothiazol-3-yl, 2,3-dihydroisothiazol-4-yl, 2,3-dihydroisothiazol-5-yl, 2,5-dihydroisothiazol-3-yl, 2,5-dihydroisothiazol-4-yl, 2,5-dihydroisothiazol-5-yl, 4,5-dihydroisothiazol-1-yl, 4,5-dihydroisothiazol-3-yl, 4,5-dihydroisothiazol-4-yl, 4,5-dihydroisothiazol-5-yl, 2,3-dihydropyrazol-3-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-4-yl, 3,4-dihydropyrazol-3-yl, 3,4-dihydropyrazol-4-yl, 3,4-dihydropyrazol-5-yl, 4,5-dihydropyrazol-4-yl, 4,5-dihydropyrazol-3-yl, 4,5-dihydropyrazol-4-yl, 4,5-dihydropyrazol-5-yl, 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-1-yl, 4,5-dihydroimidazol-2-yl, 4,5-dihydroimidazol-4-yl, 4,5-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 3,4-dihydrothiazol-2-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

six-membered partial unsaturated heterocycles like 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl.

three- to six-membered heterocyclyl: four- to six-membered heterocyclyl as mentioned above and also a monocyclic, saturated or partial unsaturated cycle having three ring members, which comprises apart from carbon atoms one nitrogen atom, one oxygen atom or one sulfur atom, for example 2-oxiranyl, 2-aziridinyl, 2-thiiranyl.

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

branched $C_4$-$C_6$-alkenyl: for example 1-methyl-1-propenyl, 2-methyl-1-propenyl, 1-methyl-2-propenyl, 2-methyl-2-propenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1propenyl, 1-ethyl-2-propenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-1-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above, and also ethynyl;

$C_1$-$C_6$-alkoxy: for example methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_6$-haloalkoxy: a $C_1$-$C_6$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkylthio: for example methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-haloalkylthio: a $C_1$-$C_6$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$-$C_6$-alkylsulfinyl ($C_1$-$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-Dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-haloalkylsulfinyl: a $C_1$-$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$-$C_6$-alkylsulfonyl ($C_1$-$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$-$C_6$-haloalkylsulfonyl: a $C_1$-$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl.

Phenyl which may be annulated with one or two more phenyl rings, for example phenyl, naphthyl and anthracenyl.

In a particular embodiment, the variables of the compounds of formula I have the following meanings, which meanings are, both on their own and in combination with one another, particular embodiments of the compounds of formula I:

Preference is given to the α-cyanoacrylates of formula I wherein $R^1$ is $OR^a$.

Preference is also given to the α-cyanoacrylates of formula I wherein $R^1$ is $OR^a$ and $R^a$ is $C_1$-$C_2$-alkyl which is partially or fully halogenated and/or carries a substituent from the group consisting of cyano, $C_3$-$C_6$-cycloalkyl, three- to six-membered heterocyclyl, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-halogenalkylsulfinyl, $C_1$-$C_6$-alkylsulfonyl and $C_1$-$C_6$-halogenalkylsulfonyl;
is branched $C_3$-$C_6$-alkyl, branched $C_4$-$C_6$-alkenyl, $C_3$-$C_6$-alkynyl, $C_3$-$C_6$-cycloalkyl or four- to six-membered heterocyclyl.

Preference is given to the α-cyanoacrylates of formula I wherein $R^1$ is $OR^a$ and $R^a$ is branched $C_3$-$C_6$-alkyl;
particularly preferably branched $C_3$-$C_4$-alkyl;
with particular preference 1-methylethyl, 2-methylpropyl or 1,1-dimethylethyl.

Preference is also given to the α-cyanoacrylates of formula I wherein $R^1$ is $OR^a$ and $R^a$ is $C_1$-$C_6$-alkyl which is partially or fully halogenated and/or carries a substituent from the group consisting of cyclopropyl, $C_2$-$C_6$-alkenyl and $C_2$-$C_6$-alkynyl;
particularly preferably branched $C_1$-$C_4$-alkyl which is partially or fully halogenated;
with particular preference ethyl or n-propyl which is partially or fully halogenated.

Preference is also given to the α-cyanoacrylates of formula I wherein $R^1$ is $OR^a$ and $R^a$ is $C_3$-$C_6$-cycloalkyl or four- to six-membered heterocyclyl;
particularly preferably $C_3$-$C_5$-cycloalkyl or four- to six-membered heterocyclyl;
with particular preference cyclopropyl, cyclopentyl or 3-oxetanyl.

Preference is also given to the α-cyanoacrylates of formula I wherein $R^1$ is $OR^a$ and
$R^2$ is $C_1$-$C_6$-alkyl which may be partially or fully halogenated and/or may carry a substituent from the group consisting of $C_1$-$C_6$-alkoxy;
  particularly preferably $C_1$-$C_4$-alkyl;
  with particular preference methyl or ethyl.
Preference is also given to the α-cyanoacrylates of formula I wherein $R^1$ is $OR^a$ and
$R^2$ is $C_1$-$C_6$-alkyl;
  with particular preference ethyl or n-propyl.
Preference is also given to the α-cyanoacrylates of formula I wherein $R^1$ is $OR^a$ and
$R^3$ is $C_1$-$C_6$-alkyl;
  particularly preferably $C_1$-$C_4$-alkyl;
  with particular preference ethyl.
Preference is also given to the α-cyanoacrylates of formula I wherein $R^1$ is $OR^a$ and
$R^3$ is $C_1$-$C_6$-alkyl which is partially or fully halogenated and/or carries a substituent from the group consisting of $C_1$-$C_6$-alkoxy;
  particularly preferably $C_1$-$C_4$-alkyl which is partially or fully halogenated and/or carries a substituent from the group consisting of $C_1$-$C_6$-alkoxy;
  with particular preference methyl or ethyl which is partially or fully halogenated and/or carries a substituent from the group consisting of $C_1$-$C_6$-alkoxy.
Preference is furthermore given to the α-cyanoacrylates of formula I wherein $R^1$ is $OR^a$ and
$R^4$ is hydrogen, fluorine, chlorine or $C_1$-$C_4$-alkyl;
  particularly preferably hydrogen, fluorine or chlorine;
  with particular preference hydrogen.
Preference is also given to the α-cyanoacrylates of formula I wherein $R^1$ is $OR^a$ and
$R^2$ is $C_1$-$C_6$-alkyl;
  with particular preference ethyl; and
$R^3$ is $C_2$-$C_6$-alkenyl or $C_2$-$C_6$-alkynyl,
  with particular preference 2-propen-1-yl or 2-propyn-1-yl.
Particular preference is given to the α-cyanoacrylates of formula I wherein $R^1$ is $OR^a$,
$R^a$ is branched $C_3$-$C_6$-alkyl;
  particularly preferably 1-methylethyl, 2-methylpropyl or 1,1-dimethylethyl;
$R^2$ is $C_1$-$C_4$-alkyl;
  particularly preferably methyl, ethyl or n-propyl;
  especially preferably methyl or ethyl;
  also especially preferably ethyl or n-propyl;
$R^3$ is $C_2$-$C_4$-alkyl;
  particularly preferably ethyl or n-propyl, especially preferably ethyl; and
$R^4$ is hydrogen, fluorine or chlorine;
  particularly preferably hydrogen.
Preference is also given to the α-cyanoacrylates of formula I wherein $R^1$ is $NR^bR^c$.
Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl.
Preference is also given to the α-cyanoacrylates of formula I wherein $R^1$ is $NR^bR^c$, where
$R^b$ is hydrogen or $C_1$-$C_6$-alkyl;
  preferably hydrogen or $C_1$-$C_4$-alkyl;
  particular preferably hydrogen, ethyl, n-propyl or i-propyl; and
$R^c$ is $C_3$-$C_6$-alkenyl or $C_3$-$C_6$-alkynyl;
  preferably $C_3$-$C_4$-alkenyl or $C_3$-$C_4$-alkynyl;
  particular preferably 1-methyl-2-propen-1-yl, 1,1-dimethyl-2-propen-1-yl; 2-propyn-1-yl or 1-methyl-2-propyn-1-yl.
Preference is also given to the α-cyanoacrylates of formula I wherein $R^1$ is $NR^bR^c$, where
$R^b$ is hydrogen or $C_1$-$C_6$-alkyl;
  preferably hydrogen or $C_1$-$C_4$-alkyl:
  particular preferably hydrogen, ethyl, n-propyl or i-propyl; and
$R^c$ is $C_3$-$C_6$-cycloalkyl or three- to six-membered heterocyclyl;
  preferably $C_3$-$C_5$-cycloalkyl or four- to six-memberd heterocyclyl;
  particular preferably cyclopropyl, cyclopentyl, 3-oxetanyl, 3-tetrahydrofuranyl or 4-tetrahydropyranyl.
Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl; and
$R^2$ is $C_1$-$C_6$-alkyl, which may be partially or fully halogenated and/or may carry a substituent from the group consisting of $C_1$-$C_6$-alkoxy;
  preferably $C_1$-$C_4$-alkyl;
  particular preferably methyl, ethyl or n-propyl.
Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl; and
$R^2$ and $R^3$ are inderpendently of each other $C_2$-$C_6$-alkyl,
  preferably $C_2$-$C_4$-alkyl,
  particular preferably ethyl.
Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl; and
$R^3$ is $C_2$-$C_6$-alkenyl or $C_2$-$C_6$-alkynyl;
  preferably $C_2$-$C_4$-alkenyl or $C_2$-$C_4$-alkynyl;
  particular preferably 2-propen-1-yl or 2-propyn-1-yl.
Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl; and
$R^4$ is hydrogen, fluorine, chlorine or $C_1$-$C_4$-alkyl;
  preferably hydrogen, fluorine or chlorine;
  particular preferably hydrogen.
Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl.

$R^2$ is $C_2$-$C_4$-alkyl;
  preferably ethyl; and
$R^3$ is $C_2$-$C_6$-alkenyl or $C_2$-$C_6$-alkynyl;
  preferably 2-propen-1-yl or 2-propyn-1-yl.
  Preference is also given to the α-cyanoacrylates of formula I wherein $R^1$ is $NR^bR^c$, where
$R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl;
$R^2$ is $C_1$-$C_4$-alkyl;
  preferably methyl, ethyl, or n-propyl;
$R^3$ is $C_2$-$C_4$-alkyl;
  preferably ethyl or n-propyl; and
$R^4$ is hydrogen.
  Preference is also given to the α-cyanoacrylates of formula I wherein $R^1$ is $SR^d$.
  Preference is also given to the α-cyanoacrylates of formula I wherein $R^1$ is $SR^d$, where
$R^d$ is hydrogen or $C_1$-$C_6$-alkyl;
  preferably hydrogen or $C_1$-$C_4$-alkyl;
  particular preferably hydrogen, ethyl, n-propyl or i-propyl.
  Preference is also given to the α-cyanoacrylates of formula I wherein $R^1$ is $SR^d$, where
$R^d$ is $C_3$-$C_6$-alkenyl or $C_3$-$C_6$-alkynyl;
  preferably $C_3$-$C_4$-alkenyl or $C_3$-$C_4$-alkynyl;
  particular preferably 1-methyl-2-propen-1-yl, 1,1-dimethyl-2-propen-1-yl; 2-propyn-1-yl or 1-methyl-2-propyn-1-yl.
  Preference is also given to the α-cyanoacrylates of formula I wherein $R^1$ is $SR^d$, where
$R^d$ is $C_3$-$C_6$-alkenyl or three- to six-memberd heterocyclyl;
  preferably $C_3$-$C_5$-cycloalkyl or four-to-six-memberd heterocyclyl;
  particular preferably cyclopropyl, cyclopentyl, 3-oxetanyl, 3-tetrahydrofuranyl or 4-tetrahydropyranyl.
  Preference is also given to the α-cyanoacrylates of formula I wherein $R^1$ is $SR^d$, where
$R^d$ is hydrogen or $C_1$-$C_6$-alkyl;
  preferably hydrogen or $C_1$-$C_4$-alkyl;
  particular preferably hydrogen, ethyl, n-propyl or i-propyl; and
$R^2$ is $C_1$-$C_6$-alkyl which may be partially or fully halogenated and/or may carry a substituent from the group consisting of $C_1$-$C_6$-alkoxy;
  preferably $C_1$-$C_4$-alkyl;
  particular preferably methyl, ethyl or n-propyl.
  Preference is also given to the α-cyanoacrylates of formula I wherein $R^1$ is $SR^d$, where
$R^d$ is hydrogen or $C_1$-$C_6$-alkyl;
  preferably hydrogen or $C_1$-$C_4$-alkyl;
  particular preferably hydrogen, ethyl, n-propyl or i-propyl; and
$R^2$ and $R^3$ are independently of each other $C_2$-$C_6$-alkyl;
  preferably $C_2$-$C_4$-alkyl;
  particular preferably ethyl.
  Preference is also given to the α-cyanoacrylates of formula I wherein $R^1$ is $SR^d$, where
$R^d$ is hydrogen or $C_1$-$C_6$-alkyl;
  preferably hydrogen or $C_1$-$C_4$-alkyl;
  particular preferably hydrogen, ethyl, n-propyl or i-propyl; and
$R^3$ is $C_2$-$C_6$-alkenyl or $C_2$-$C_6$-alkynyl;
  preferably $C_2$-$C_4$-alkenyl or $C_2$-$C_6$-alkynyl;
  particular preferably 2-propen-1-yl or 2-propyn-1-yl.
  Preference is also given to the α-cyanoacrylates of formula I wherein $R^1$ is $SR^d$, where
$SR^d$ is hydrogen or $C_1$-$C_6$-alkyl;
  preferably hydrogen or $C_1$-$C_4$-alkyl;
  particular preferably hydrogen, ethyl, n-propyl or i-propyl; and
$R^4$ is hydrogen, fluorine, chlorine or $C_1$-$C_4$-alkyl;
  preferably hydrogen, fluorine or chlorine;
  particular preferably hydrogen.
  Preference is also given to the α-cyanoacrylates of formula I wherein $R^1$ is $SR^d$, where
$SR^d$ is hydrogen or $C_1$-$C_6$-alkyl;
  preferably hydrogen or $C_1$-$C_4$-alkyl;
  particular preferably hydrogen, ethyl, n-propyl or i-propyl; and
$R^2$ is $C_2$-$C_4$-alkyl;
  preferably ethyl; and
$R^3$ is $C_2$-$C_6$-alkenyl or $C_2$-$C_6$-alkenyl;
  preferably 2-propen-1-yl or 2-propyn-1-yl.
  Preference is also given to the α-cyanoacrylates of formula I wherein $R^1$ is $SR^d$, where
$R^d$ is hydrogen or $C_1$-$C_6$-alkyl;
  preferably hydrogen or $C_1$-$C_4$-alkyl;
  particular preferably hydrogen, ethyl, n-propyl or i-propyl; and
$R^2$ is $C_1$-$C_4$-alkyl;
  preferably methyl, ethyl, or n-propyl;
$R^3$ is $C_2$-$C_4$-alkyl;
  preferably ethyl, or n-propyl; and
$R^4$ is hydrogen.
  Extraordinary preference is given to the compounds of formula I.1 (corresponds to formula I where $R^1$ is $OR^a$ wherein $R^a$ is i-$C_3H_7$ and $R^4$ is H), in particular to the compounds of formulae I.1.1 to I.1.79 of table 1, where the definitions of the variables $R^1$ to $R^4$ are of particular importance for the compounds according to the invention not only in combination with one another, but in each case also on their own.

TABLE 1

I.1 structure with $R^2$, $R^3$, $NH_2$, CN, C(O)O-i$C_3H_7$, H

| No. | $R^2$ | $R^3$ |
|---|---|---|
| I.1.1 | $CH_3$ | $CH_3$ |
| I.1.2 | $CH_3$ | $C_2H_5$ |
| I.1.3 | $CH_3$ | $nC_3H_7$ |
| I.1.4 | $CH_3$ | $iC_3H_7$ |
| I.1.5 | $CH_3$ | $nC_4H_9$ |
| I.1.6 | $CH_3$ | $CH_2CH(CH_3)_2$ |
| I.1.7 | $CH_3$ | $CH(CH_3)C_2H_5$ |
| I.1.8 | $CH_3$ | $tC_4H_9$ |
| I.1.9 | $C_2H_5$ | $C_2H_5$ |
| I.1.10 | $C_2H_5$ | $nC_3H_7$ |
| I.1.11 | $C_2H_5$ | $iC_3H_7$ |
| I.1.12 | $C_2H_5$ | $nC_4H_9$ |
| I.1.13 | $C_2H_5$ | $CH_2CH(CH_3)_2$ |
| I.1.14 | $C_2H_5$ | $CH(CH_3)C_2H_5$ |
| I.1.15 | $C_2H_5$ | $tC_4H_9$ |
| I.1.16 | $nC_3H_7$ | $nC_3H_7$ |
| I.1.17 | $nC_3H_7$ | $iC_3H_7$ |

TABLE 1-continued

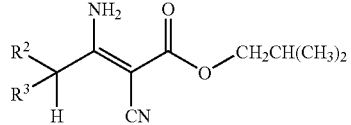

I.1

| No. | $R^2$ | $R^3$ |
|---|---|---|
| I.1.18 | $iC_3H_7$ | $iC_3H_7$ |
| I.1.19 | $CH_2F$ | $CH_3$ |
| I.1.20 | $CH_2F$ | $C_2H_5$ |
| I.1.21 | $CH_2F$ | $CH_2F$ |
| I.1.22 | $CH_2Cl$ | $CH_3$ |
| I.1.23 | $CH_2Cl$ | $C_2H_5$ |
| I.1.24 | $CH_2Cl$ | $CH_2Cl$ |
| I.1.25 | $CH_2Br$ | $CH_3$ |
| I.1.26 | $CH_2Br$ | $C_2H_5$ |
| I.1.27 | $CH_2Br$ | $CH_2Br$ |
| I.1.28 | $CHF_2$ | $CH_3$ |
| I.1.29 | $CHF_2$ | $C_2H_5$ |
| I.1.30 | $CHF_2$ | $CHF_2$ |
| I.1.31 | $CF_3$ | $CH_3$ |
| I.1.32 | $CF_3$ | $C_2H_5$ |
| I.1.33 | $CF_3$ | $CF_3$ |
| I.1.34 | $(CH_2)_2F$ | $CH_3$ |
| I.1.35 | $(CH_2)_2F$ | $C_2H_5$ |
| I.1.36 | $(CH_2)_2F$ | $(CH_2)_2F$ |
| I.1.37 | $(CH_2)_2Cl$ | $CH_3$ |
| I.1.38 | $(CH_2)_2Cl$ | $C_2H_5$ |
| I.1.39 | $(CH_2)_2Cl$ | $(CH_2)_2Cl$ |
| I.1.40 | $(CH_2)_2Br$ | $CH_3$ |
| I.1.41 | $(CH_2)_2Br$ | $C_2H_5$ |
| I.1.42 | $(CH_2)_2Br$ | $(CH_2)_2Br$ |
| I.1.43 | $CH_2CF_3$ | $CH_3$ |
| I.1.44 | $CH_2CF_3$ | $C_2H_5$ |
| I.1.45 | $CH_2CF_3$ | $CH_2CF_3$ |
| I.1.46 | $CH_2OCH_3$ | $CH_3$ |
| I.1.47 | $CH_2OCH_3$ | $C_2H_5$ |
| I.1.48 | $CH_2OCH_3$ | $CH_2OCH_3$ |
| I.1.49 | $(CH_2)_2OCH_3$ | $CH_3$ |
| I.1.50 | $(CH_2)_2OCH_3$ | $C_2H_5$ |
| I.1.51 | $(CH_2)_2OCH_3$ | $(CH_2)_2OCH_3$ |
| I.1.52 | $(CH_2)_3OCH_3$ | $CH_3$ |
| I.1.53 | $(CH_2)_3OCH_3$ | $C_2H_5$ |
| I.1.54 | $(CH_2)_3OCH_3$ | $(CH_2)_3OCH_3$ |
| I.1.55 | $CH(CH_3)CH_2OCH_3$ | $CH_3$ |
| I.1.56 | $CH(CH_3)CH_2OCH_3$ | $C_2H_5$ |
| I.1.57 | $CH(CH_3)CH_2OCH_3$ | $CH(CH_3)CH_2OCH_3$ |
| I.1.58 | $CH_2CH(CH_3)OCH_3$ | $CH_3$ |
| I.1.59 | $CH_2CH(CH_3)OCH_3$ | $C_2H_5$ |
| I.1.60 | $CH_2CH(CH_3)OCH_3$ | $CH_2CH(CH_3)OCH_3$ |
| I.1.61 | $CH_2OC_2H_5$ | $CH_3$ |
| I.1.62 | $CH_2OC_2H_5$ | $C_2H_5$ |
| I.1.63 | $CH_2OC_2H_5$ | $CH_2OC_2H_5$ |
| I.1.64 | $(CH_2)_2OC_2H_5$ | $CH_3$ |
| I.1.65 | $(CH_2)_2OC_2H_5$ | $C_2H_5$ |
| I.1.66 | $(CH_2)_2OC_2H_5$ | $(CH_2)_2OC_2H_5$ |
| I.1.67 | $(CH_2)_3OC_2H_5$ | $CH_3$ |
| I.1.68 | $(CH_2)_3OC_2H_5$ | $C_2H_5$ |
| I.1.69 | $(CH_2)_3OC_2H_5$ | $(CH_2)_3OC_2H_5$ |
| I.1.70 | $CH(CH_3)CH_2OC_2H_5$ | $CH_3$ |
| I.1.71 | $CH(CH_3)CH_2OC_2H_5$ | $C_2H_5$ |
| I.1.72 | $CH(CH_3)CH_2OC_2H_5$ | $CH(CH_3)CH_2OC_2H_5$ |
| I.1.73 | $CH_2CH(CH_3)OC_2H_5$ | $CH_3$ |
| I.1.74 | $CH_2CH(CH_3)OC_2H_5$ | $C_2H_5$ |
| I.1.75 | $CH_2CH(CH_3)OC_2H_5$ | $CH_2CH(CH_3)OC_2H_5$ |
| I.1.76 | $CH_2CH=CH_2$ | $C_2H_5$ |
| I.1.77 | $CH_2CH=CH_2$ | $CH_2CH=CH_2$ |
| I.1.78 | $CH_2CH=CH_2$ | $CH_2C\equiv CH$ |
| I.1.79 | $CH_2C\equiv CH$ | $CH_2C\equiv CH$ |

Extraordinary preference is also given to the compounds of formula I.2, in particular to the compounds of formulae I.2.1 to I.2.79 which differ from the corresponding compounds of formulae I.1.1 to I.1.79 in that $R^a$ is $CH_2CH(CH_3)_2$.

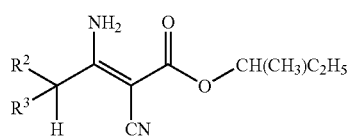

Extraordinary preference is also given to the compounds of formula I.3, in particular to the compounds of formulae I.3.1 to I.3.79, which differ from the corresponding compounds of formulae I.1.1 to I.1.79 in that $R^a$ is $CH(CH_3)C_2H_5$.

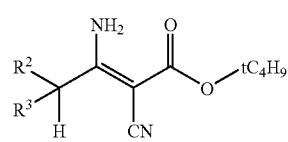

Extraordinary preference is also given to the compounds of formula I.4, in particular to the compounds of formulae I.4.1 to I.4.79, which differ from the corresponding compounds of formulae I.1.1 to I.1.79 in that $R^a$ is $tC_4H_9$.

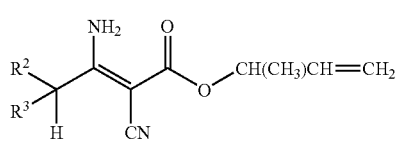

Extraordinary preference is also given to the compounds of formula I.5, in particular to the compounds of formulae I.5.1 to I.5.79, which differ from the corresponding compounds of formulae I.1.1 to I.1.79 in that $R^a$ is $CH(CH_3)CH=CH_2$.

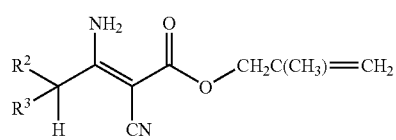

Extraordinary preference is also given to the compounds of formula I.6, in particular to the compounds of formulae I.6.1 to I.6.79, which differ from the corresponding compounds of formulae I.1.1 to I.1.79 in that $R^a$ is $CH_2C(CH_3)=CH_2$.

Extraordinary preference is also given to the compounds of formula I.7, in particular to the compounds of formulae I.7.1 to I.7.79, which differ from the corresponding compounds of formulae I.1.1 to I.1.79 in that $R^a$ is $CH(CH_3)CH=CHCH_3$.

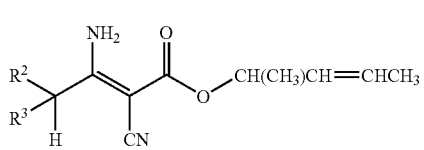

I.7

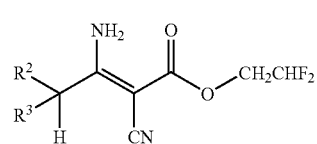

I.12

Extraordinary preference is also given to the compounds of formula I.8, in particular to the compounds of formulae I.8.1 to I.8.79, which differ from the corresponding compounds of formulae I.1.1 to I.1.79 in that $R^a$ is $CH_2CCH$.

Extraordinary preference is also given to the compounds of formula I.13, in particular to the compounds of formulae I.13.1 to I.13.79, which differ from the corresponding compounds of formulae I.1.1 to I.1.79 in that $R^a$ is $CH_2CF_3$.

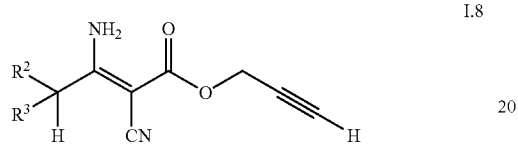

I.8

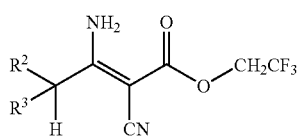

I.13

Extraordinary preference is also given to the compounds of formula I.9, in particular to the compounds of formulae I.9.1 to I.9.79, which differ from the corresponding compounds of formulae I.1.1 to I.1.79 in that $R^a$ is $CHCH_3CCH$.

Extraordinary preference is also given to the compounds of formula I.14, in particular to the compounds of formulae I.14.1 to I.14.79, which differ from the corresponding compounds of formulae I.1.1 to I.1.79 in that $R^a$ is $(CH_2)_2CH_2F$.

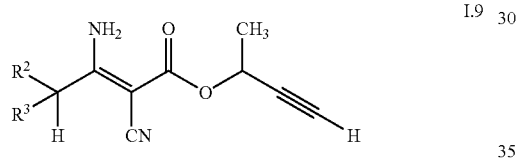

I.9

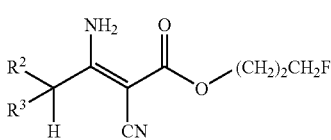

I.14

Extraordinary preference is also given to the compounds of formula I.10, in particular to the compounds of formulae I.10.1 to I.10.79, which differ from the corresponding compounds of formulae I.1.1 to I.1.79 in that $R^a$ is $CH_2CCCH_3$.

Extraordinary preference is also given to the compounds of formula I.15, in particular to the compounds of formulae I.15.1 to I.15.79, which differ from the corresponding compounds of formulae I.1.1 to I.1.79 in that $R^a$ is $(CH_2)_2CF_3$.

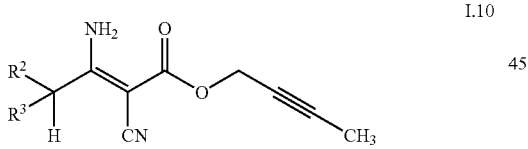

I.10

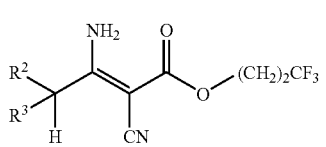

I.15

Extraordinary preference is also given to the compounds of formula I.11, in particular to the compounds of formulae I.11.1 to I.11.79, which differ from the corresponding compounds of formulae I.1.1 to I.1.79 in that $R^a$ is $(CH_2)_2CCH$.

Extraordinary preference is also given to the compounds of formula I.16, in particular to the compounds of formulae I.16.1 to I.16.79, which differ from the corresponding compounds of formulae I.1.1 to I.1.79 in that $R^a$ is $CH_2CHCl_2$.

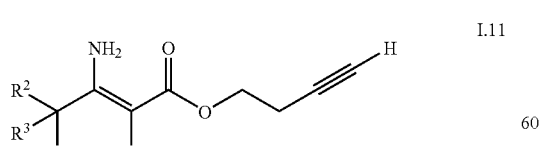

I.11

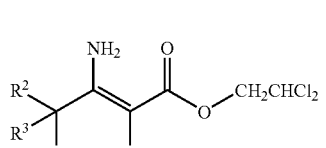

I.16

Extraordinary preference is also given to the compounds of formula I.12, in particular to the compounds of formulae I.12.1 to I.12.79, which differ from the corresponding compounds of formulae I.1.1 to I.1.79 in that $R^a$ is $CH_2CHF_2$.

Extraordinary preference is also given to the compounds of formula I.17, in particular to the compounds of formulae I.17.1 to I.17.79, which differ from the corresponding compounds of formulae I.1.1 to I.1.79 in that $R^a$ is $CH_2CCl_3$.

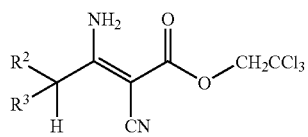

I.17

Extraordinary preference is also given to the compounds of formula I.18, in particular to the compounds of formulae I.18.1 to I.18.79, which differ from the corresponding compounds of formulae I.1.1 to I.1.79 in that $R^a$ is $(CH_2)_2CH_2Cl$.

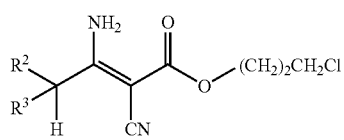

I.18

Extraordinary preference is also given to the compounds of formula I.19, in particular to the compounds of formulae I.19.1 to I.19.79, which differ from the corresponding compounds of formulae I.1.1 to I.1.79 in that $R^a$ is $(CH_2)_2CCl_3$.

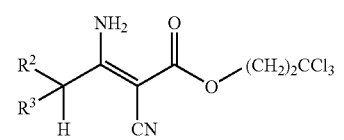

I.19

Extraordinary preference is also given to the compounds of formula I.20, in particular to the compounds of formulae I.20.1 to I.20.79, which differ from the corresponding compounds of formulae I.1.1 to I.1.79 in that $R^a$ is $CH_2CHBr_2$.

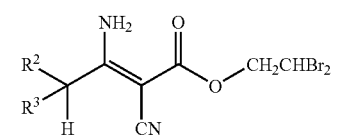

I.20

Extraordinary preference is also given to the compounds of formula I.21, in particular to the compounds of formulae I.21.1 to I.21.79, which differ from the corresponding compounds of formulae I.1.1 to I.1.79 in that $R^a$ is $CH_2CBr_3$.

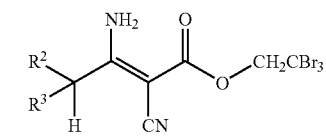

I.21

Extraordinary preference is also given to the compounds of formula I.22, in particular to the compounds of formulae I.22.1 to I.22.79, which differ from the corresponding compounds of formulae I.1.1 to I.1.79 in that $R^a$ is $(CH_2)_2CH_2Br$.

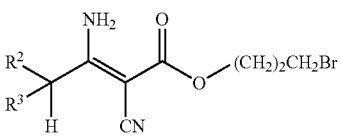

I.22

Extraordinary preference is also given to the compounds of formula I.23, in particular to the compounds of formulae I.23.1 to I.23.79, which differ from the corresponding compounds of formulae I.1.1 to I.1.79 in that $R^a$ is $(CH_2)_2CBr_3$.

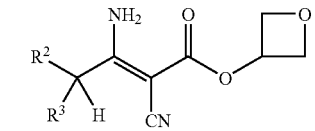

I.23

Extraordinary preference is also given to the compounds of formula I.24, in particular to the compounds of formulae I.24.1 to I.24.79, which differ from the corresponding compounds of formulae I.1.1 to I.1.79 in that $R^a$ is 3-oxetanyl.

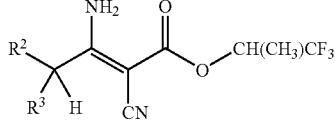

I.24

Extraordinary preference is also given to the compounds of formula I.25, in particular to the compounds of formulae I.2$_5$.1 to I.2$_5$.79, which differ from the corresponding compounds of formulae I.1.1 to I.1.79 in that $R^a$ is $CH(CH_3)CF_3$.

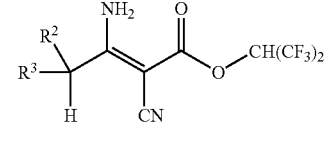

I.25

Extraordinary preference is also given to the compounds of formula I.26, in particular to the compounds of formulae I.26.1 to I.26.79, which differ from the corresponding compounds of formulae I.1.1 to I.1.79 in that $R^a$ is $CH(CF_3)_2$.

I.26

Extraordinary preference is also given to the compounds of formula I.27 (corresponds to formula I wherein $R^1$ is $NR^bR^c$ with $R^c$ is hydrogen and $R^4$ is hydrogen), in particular to the compounds of formulae I.27.1 to I.27.180 of table 2, where the definitions of the variables $R_1$ to $R_4$ are of particular importance for the compounds according to the inventions not only in combination with one another, but each case on their own.

TABLE 2

I.27

$$\text{Structure: } R^2R^3CH-C(NH_2)=C(CN)-C(O)-NH-R^b$$

| No. | $R^b$ | $R^2$ | $R^3$ |
|---|---|---|---|
| I.27.1 | H | $C_2H_5$ | $C_2H_5$ |
| I.27.2 | H | $C_2H_5$ | $nC_3H_7$ |
| I.27.3 | H | $C_2H_5$ | $iC_3H_7$ |
| I.27.4 | H | $C_2H_5$ | $nC_4H_9$ |
| I.27.5 | H | $C_2H_5$ | $CH_2CH(CH_3)_2$ |
| I.27.6 | H | $C_2H_5$ | $CH(CH_3)C_2C_5$ |
| I.27.7 | H | $C_2H_5$ | $CH_2CH=CH_2$ |
| I.27.8 | H | $C_2H_5$ | $CH_2C\equiv CH$ |
| I.27.9 | H | $nC_3H_7$ | $nC_3H_7$ |
| I.27.10 | H | $nC_3H_7$ | $iC_3H_7$ |
| I.27.11 | H | $nC_3H_7$ | $nC_4H_9$ |
| I.27.12 | H | $nC_3H_7$ | $CH_2CH(CH_3)_2$ |
| I.27.13 | H | $nC_3H_7$ | $CH(CH_3)C_2C_5$ |
| I.27.14 | H | $nC_3H_7$ | $CH_2CH=CH_2$ |
| I.27.15 | H | $nC_3H_7$ | $CH_2C\equiv CH$ |
| I.27.16 | H | $iC_3H_7$ | $iC_3H_7$ |
| I.27.17 | H | $iC_3H_7$ | $nC_4H_9$ |
| I.27.18 | H | $iC_3H_7$ | $CH_2CH(CH_3)_2$ |
| I.27.19 | H | $iC_3H_7$ | $CH(CH_3)C_2C_5$ |
| I.27.20 | H | $iC_3H_7$ | $CH_2CH=CH_2$ |
| I.27.21 | H | $iC_3H_7$ | $CH_2C\equiv CH$ |
| I.27.22 | H | $nC_4H_9$ | $nC_4H_9$ |
| I.27.23 | H | $nC_4H_9$ | $CH_2CH(CH_3)_2$ |
| I.27.24 | H | $nC_4H_9$ | $CH(CH_3)C_2C_5$ |
| I.27.25 | H | $nC_4H_9$ | $CH_2CH=CH_2$ |
| I.27.26 | H | $nC_4H_9$ | $CH_2C\equiv CH$ |
| I.27.27 | H | $CH_2CH(CH_3)_2$ | $CH_2CH(CH_3)_2$ |
| I.27.28 | H | $CH_2CH(CH_3)_2$ | $CH(CH_3)C_2C_5$ |
| I.27.29 | H | $CH_2CH(CH_3)_2$ | $CH_2CH=CH_2$ |
| I.27.30 | H | $CH_2CH(CH_3)_2$ | $CH_2C\equiv CH$ |
| I.27.31 | H | $CH(CH_3)C_2C_5$ | $CH(CH_3)C_2C_5$ |
| I.27.32 | H | $CH(CH_3)C_2C_5$ | $CH_2CH=CH_2$ |
| I.27.33 | H | $CH(CH_3)C_2C_5$ | $CH_2C\equiv CH$ |
| I.27.34 | H | $CH_2CH=CH_2$ | $CH_2CH=CH_2$ |
| I.27.35 | H | $CH_2CH=CH_2$ | $CH_2C\equiv CH$ |
| I.27.36 | H | $CH_2C\equiv CH$ | $CH_2C\equiv CH$ |
| I.27.37 | $CH_3$ | $C_2H_5$ | $C_2H_5$ |
| I.27.38 | $CH_3$ | $C_2H_5$ | $nC_3H_7$ |
| I.27.39 | $CH_3$ | $C_2H_5$ | $iC_3H_7$ |
| I.27.40 | $CH_3$ | $C_2H_5$ | $nC_4H_9$ |
| I.27.41 | $CH_3$ | $C_2H_5$ | $CH_2CH(CH_3)_2$ |
| I.27.42 | $CH_3$ | $C_2H_5$ | $CH(CH_3)C_2C_5$ |
| I.27.43 | $CH_3$ | $C_2H_5$ | $CH_2CH=CH_2$ |
| I.27.44 | $CH_3$ | $C_2H_5$ | $CH_2C\equiv CH$ |
| I.27.45 | $CH_3$ | $nC_3H_7$ | $nC_3H_7$ |
| I.27.46 | $CH_3$ | $nC_3H_7$ | $iC_3H_7$ |
| I.27.47 | $CH_3$ | $nC_3H_7$ | $nC_4H_9$ |
| I.27.48 | $CH_3$ | $nC_3H_7$ | $CH_2CH(CH_3)_2$ |
| I.27.49 | $CH_3$ | $nC_3H_7$ | $CH(CH_3)C_2C_5$ |
| I.27.50 | $CH_3$ | $nC_3H_7$ | $CH_2CH=CH_2$ |
| I.27.51 | $CH_3$ | $nC_3H_7$ | $CH_2C\equiv CH$ |
| I.27.52 | $CH_3$ | $iC_3H_7$ | $iC_3H_7$ |
| I.27.53 | $CH_3$ | $iC_3H_7$ | $nC_4H_9$ |
| I.27.54 | $CH_3$ | $iC_3H_7$ | $CH_2CH(CH_3)_2$ |
| I.27.55 | $CH_3$ | $iC_3H_7$ | $CH(CH_3)C_2C_5$ |
| I.27.56 | $CH_3$ | $iC_3H_7$ | $CH_2CH=CH_2$ |
| I.27.57 | $CH_3$ | $iC_3H_7$ | $CH_2C\equiv CH$ |
| I.27.58 | $CH_3$ | $nC_4H_9$ | $nC_4H_9$ |
| I.27.59 | $CH_3$ | $nC_4H_9$ | $CH_2CH(CH_3)_2$ |
| I.27.60 | $CH_3$ | $nC_4H_9$ | $CH(CH_3)C_2C_5$ |
| I.27.61 | $CH_3$ | $nC_4H_9$ | $CH_2CH=CH_2$ |
| I.27.62 | $CH_3$ | $nC_4H_9$ | $CH_2C\equiv CH$ |
| I.27.63 | $CH_3$ | $CH_2CH(CH_3)_2$ | $CH_2CH(CH_3)_2$ |
| I.27.64 | $CH_3$ | $CH_2CH(CH_3)_2$ | $CH(CH_3)C_2C_5$ |
| I.27.65 | $CH_3$ | $CH_2CH(CH_3)_2$ | $CH_2CH=CH_2$ |
| I.27.66 | $CH_3$ | $CH_2CH(CH_3)_2$ | $CH_2C\equiv CH$ |
| I.27.67 | $CH_3$ | $CH(CH_3)C_2C_5$ | $CH(CH_3)C_2C_5$ |
| I.27.68 | $CH_3$ | $CH(CH_3)C_2C_5$ | $CH_2CH=CH_2$ |
| I.27.69 | $CH_3$ | $CH(CH_3)C_2C_5$ | $CH_2C\equiv CH$ |
| I.27.70 | $CH_3$ | $CH_2CH=CH_2$ | $CH_2CH=CH_2$ |
| I.27.71 | $CH_3$ | $CH_2CN=CH_2$ | $CH_2C\equiv CH$ |
| I.27.72 | $CH_3$ | $CH_2C\equiv CH$ | $CH_2C\equiv CH$ |
| I.27.73 | $C_2H_5$ | $C_2H_5$ | $C_2H_5$ |
| I.27.74 | $C_2H_5$ | $C_2H_5$ | $nC_3H_7$ |
| I.27.75 | $C_2H_5$ | $C_2H_5$ | $iC_3H_7$ |
| I.27.76 | $C_2H_5$ | $C_2H_5$ | $nC_4H_9$ |
| I.27.77 | $C_2H_5$ | $C_2H_5$ | $CH_2CH(CH_3)_2$ |
| I.27.78 | $C_2H_5$ | $C_2H_5$ | $CH(CH_3)C_2C_5$ |
| I.27.79 | $C_2H_5$ | $C_2H_5$ | $CH_2CH=CH_2$ |
| I.27.80 | $C_2H_5$ | $C_2H_5$ | $CH_2C\equiv CH$ |
| I.27.81 | $C_2H_5$ | $nC_3H_7$ | $nC_3H_7$ |
| I.27.82 | $C_2H_5$ | $nC_3H_7$ | $iC_3H_7$ |
| I.27.83 | $C_2H_5$ | $nC_3H_7$ | $nC_4H_9$ |
| I.27.84 | $C_2H_5$ | $nC_3H_7$ | $CH_2CH(CH_3)_2$ |
| I.27.85 | $C_2H_5$ | $nC_3H_7$ | $CH(CH_3)C_2C_5$ |
| I.27.86 | $C_2H_5$ | $nC_3H_7$ | $CH_2CH=CH_2$ |
| I.27.87 | $C_2H_5$ | $nC_3H_7$ | $CH_2C\equiv CH$ |
| I.27.88 | $C_2H_5$ | $iC_3H_7$ | $iC_3H_7$ |
| I.27.89 | $C_2H_5$ | $iC_3H_7$ | $nC_4H_9$ |
| I.27.90 | $C_2H_5$ | $iC_3H_7$ | $CH_2CH(CH_3)_2$ |
| I.27.91 | $C_2H_5$ | $iC_3H_7$ | $CH(CH_3)C_2C_5$ |
| I.27.92 | $C_2H_5$ | $iC_3H_7$ | $CH_2CH=CH_2$ |
| I.27.93 | $C_2H_5$ | $iC_3H_7$ | $CH_2C\equiv CH$ |
| I.27.94 | $C_2H_5$ | $nC_4H_9$ | $nC_4H_9$ |
| I.27.95 | $C_2H_5$ | $nC_4H_9$ | $CH_2CH(CH_3)_2$ |
| I.27.96 | $C_2H_5$ | $nC_4H_9$ | $CH(CH_3)C_2C_5$ |
| I.27.97 | $C_2H_5$ | $nC_4H_9$ | $CH_2CH=CH_2$ |
| I.27.98 | $C_2H_5$ | $nC_4H_9$ | $CH_2C\equiv CH$ |
| I.27.99 | $C_2H_5$ | $CH_2CH(CH_3)_2$ | $CH_2CH(CH_3)_2$ |
| I.27.100 | $C_2H_5$ | $CH_2CH(CH_3)_2$ | $CH(CH_3)C_2C_5$ |
| I.27.101 | $C_2H_5$ | $CH_2CH(CH_3)_2$ | $CH_2CH=CH_2$ |
| I.27.102 | $C_2H_5$ | $CH_2CH(CH_3)_2$ | $CH_2C\equiv CH$ |
| I.27.103 | $C_2H_5$ | $CH(CH_3)C_2C_5$ | $CH(CH_3)C_2C_5$ |
| I.27.104 | $C_2H_5$ | $CH(CH_3)C_2C_5$ | $CH_2CH=CH_2$ |
| I.27.105 | $C_2H_5$ | $CH(CH_3)C_2C_5$ | $CH_2C\equiv CH$ |
| I.27.106 | $C_2H_5$ | $CH_2CH=CH_2$ | $CH_2CH=CH_2$ |
| I.27.107 | $C_2H_5$ | $CH_2CH=CH_2$ | $CH_2C\equiv CH$ |
| I.27.108 | $C_2H_5$ | $CH_2C\equiv CH$ | $CH_2C\equiv CH$ |
| I.27.109 | $nC_3H_7$ | $C_2H_5$ | $C_2H_5$ |
| I.27.110 | $nC_3H_7$ | $C_2H_5$ | $nC_3H_7$ |
| I.27.111 | $nC_3H_7$ | $C_2H_5$ | $iC_3H_7$ |
| I.27.112 | $nC_3H_7$ | $C_2H_5$ | $nC_4H_9$ |
| I.27.113 | $nC_3H_7$ | $C_2H_5$ | $CH_2CH(CH_3)_2$ |
| I.27.114 | $nC_3H_7$ | $C_2H_5$ | $CH(CH_3)C_2C_5$ |
| I.27.115 | $nC_3H_7$ | $C_2H_5$ | $CH_2CH=CH_2$ |
| I.27.116 | $nC_3H_7$ | $C_2H_5$ | $CH_2C\equiv CH$ |
| I.27.117 | $nC_3H_7$ | $nC_3H_7$ | $nC_3H_7$ |
| I.27.118 | $nC_3H_7$ | $nC_3H_7$ | $iC_3H_7$ |
| I.27.119 | $nC_3H_7$ | $nC_3H_7$ | $nC_4H_9$ |
| I.27.120 | $nC_3H_7$ | $nC_3H_7$ | $CH_2CH(CH_3)_2$ |
| I.27.121 | $nC_3H_7$ | $nC_3H_7$ | $CH(CH_3)C_2C_5$ |
| I.27.122 | $nC_3H_7$ | $nC_3H_7$ | $CH_2CH=CH_2$ |
| I.27.123 | $nC_3H_7$ | $nC_3H_7$ | $CH_2C\equiv CH$ |
| I.27.124 | $nC_3H_7$ | $iC_3H_7$ | $iC_3H_7$ |
| I.27.125 | $nC_3H_7$ | $iC_3H_7$ | $nC_4H_9$ |
| I.27.126 | $nC_3H_7$ | $iC_3H_7$ | $CH_2CH(CH_3)_2$ |
| I.27.127 | $nC_3H_7$ | $iC_3H_7$ | $CH(CH_3)C_2C_5$ |
| I.27.128 | $nC_3H_7$ | $iC_3H_7$ | $CH_2CH=CH_2$ |
| I.27.129 | $nC_3H_7$ | $iC_3H_7$ | $CH_2C\equiv CH$ |
| I.27.130 | $nC_3H_7$ | $nC_4H_9$ | $nC_4H_9$ |
| I.27.131 | $nC_3H_7$ | $nC_4H_9$ | $CH_2CH(CH_3)_2$ |
| I.27.132 | $nC_3H_7$ | $nC_4H_9$ | $CH(CH_3)C_2C_5$ |
| I.27.133 | $nC_3H_7$ | $nC_4H_9$ | $CH_2CH=CH_2$ |
| I.27.134 | $nC_3H_7$ | $nC_4H_9$ | $CH_2C\equiv CH$ |

TABLE 2-continued

I.27 structure with R², R³, NH₂, CN, C(O)NHR^b

| No. | R^b | R² | R³ |
|---|---|---|---|
| I.27.135 | nC₃H₇ | CH₂CH(CH₃)₂ | CH₂CH(CH₃)₂ |
| I.27.136 | nC₃H₇ | CH₂CH(CH₃)₂ | CH(CH₃)C₂C₅ |
| I.27.137 | nC₃H₇ | CH₂CH(CH₃)₂ | CH₂CH=CH₂ |
| I.27.138 | nC₃H₇ | CH₂CH(CH₃)₂ | CH₂C≡CH |
| I.27.139 | nC₃H₇ | CH(CH₃)C₂C₅ | CH(CH₃)C₂C₅ |
| I.27.140 | nC₃H₇ | CH(CH₃)C₂C₅ | CH₂CH=CH₂ |
| I.27.141 | nC₃H₇ | CH(CH₃)C₂C₅ | CH₂C≡CH |
| I.27.142 | nC₃H₇ | CH₂CH=CH₂ | CH₂CH=CH₂ |
| I.27.143 | nC₃H₇ | CH₂CH=CH₂ | CH₂C≡CH |
| I.27.144 | nC₃H₇ | CH₂C≡CH | CH₂C≡CH |
| I.27.145 | iC₃H₇ | C₂H₅ | C₂H₅ |
| I.27.146 | iC₃H₇ | C₂H₅ | nC₃H₇ |
| I.27.147 | iC₃H₇ | C₂H₅ | iC₃H₇ |
| I.27.148 | iC₃H₇ | C₂H₅ | nC₄H₉ |
| I.27.149 | iC₃H₇ | C₂H₅ | CH₂CH(CH₃)₂ |
| I.27.150 | iC₃H₇ | C₂H₅ | CH(CH₃)C₂C₅ |
| I.27.151 | iC₃H₇ | C₂H₅ | CH₂CH=CH₂ |
| I.27.152 | iC₃H₇ | C₂H₅ | CH₂C≡CH |
| I.27.153 | iC₃H₇ | nC₃H₇ | nC₃H₇ |
| I.27.154 | iC₃H₇ | nC₃H₇ | iC₃H₇ |
| I.27.155 | iC₃H₇ | nC₃H₇ | nC₄H₉ |
| I.27.156 | iC₃H₇ | nC₃H₇ | CH₂CH(CH₃)₂ |
| I.27.157 | iC₃H₇ | nC₃H₇ | CH(CH₃)C₂C₅ |
| I.27.158 | iC₃H₇ | nC₃H₇ | CH₂CH=CH₂ |
| I.27.159 | iC₃H₇ | nC₃H₇ | CH₂C≡CH |
| I.27.160 | iC₃H₇ | iC₃H₇ | iC₃H₇ |
| I.27.161 | iC₃H₇ | iC₃H₇ | nC₄H₉ |
| I.27.162 | iC₃H₇ | iC₃H₇ | CH₂CH(CH₃)₂ |
| I.27.163 | iC₃H₇ | iC₃H₇ | CH(CH₃)C₂C₅ |
| I.27.164 | iC₃H₇ | iC₃H₇ | CH₂CH=CH₂ |
| I.27.165 | iC₃H₇ | iC₃H₇ | CH₂C≡CH |
| I.27.166 | iC₃H₇ | nC₄H₉ | nC₄H₉ |
| I.27.167 | iC₃H₇ | nC₄H₉ | CH₂CH(CH₃)₂ |
| I.27.168 | iC₃H₇ | nC₄H₉ | CH(CH₃)C₂C₅ |
| I.27.169 | iC₃H₇ | nC₄H₉ | CH₂CH=CH₂ |
| I.27.170 | iC₃H₇ | nC₄H₉ | CH₂C≡CH |
| I.27.171 | iC₃H₇ | CH₂CH(CH₃)₂ | CH₂CH(CH₃)₂ |
| I.27.172 | iC₃H₇ | CH₂CH(CH₃)₂ | CH(CH₃)C₂C₅ |
| I.27.173 | iC₃H₇ | CH₂CH(CH₃)₂ | CH₂CH=CH₂ |
| I.27.174 | iC₃H₇ | CH₂CH(CH₃)₂ | CH₂C≡CH |
| I.27.175 | iC₃H₇ | CH(CH₃)C₂C₅ | CH(CH₃)C₂C₅ |
| I.27.176 | iC₃H₇ | CH(CH₃)C₂C₅ | CH₂CH=CH₂ |
| I.27.177 | iC₃H₇ | CH(CH₃)C₂C₅ | CH₂C≡CH |
| I.27.178 | iC₃H₇ | CH₂CH=CH₂ | CH₂CH=CH₂ |
| I.27.179 | iC₃H₇ | CH₂CH=CH₂ | CH₂C≡CH |
| I.27.180 | iC₃H₇ | CH₂C≡CH | CH₂C≡CH |

Extraordinary preference is also given to the compounds of formula I.28, in particular to the compounds of formulae I.28.1 to I.28.180, which differ from the corresponding compounds of formulae I.27.1 to I.27.180 in that $R^c$ is $CH_3$.

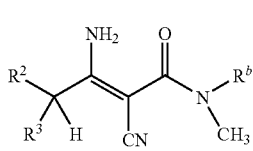

I.28

Extraordinary preference is also given to the compounds of formula I.29, in particular to the compounds of formulae I.29.1 to I.29.180, which differ from the corresponding compounds of formulae I.27.1 to I.27.180 in that $R^c$ is $C_2H_5$.

I.29

Extraordinary preference is also given to the compounds of formula I.30, in particular to the compounds of formulae I.30.1 to I.30.180, which differ from the corresponding compounds of formulae I.27.1 to I.27.180 in that $R^c$ is $nC_3H_7$.

I.30

Extraordinary preference is also given to the compounds of formula I.31, in particular to the compounds of formulae I.31.1 to I.31.180, which differ from the corresponding compounds of formulae I.27.1 to I.27.180 in that $R^c$ is $iC_3H_7$.

I.31

Extraordinary preference is also given to the compounds of formula I.32, in particular to the compounds of formulae I.32.1 to I.32.180, which differ from the corresponding compounds of formulae I.27.1 to I.27.180 in that $R^c$ is $CH_2CH(CH_3)_2$.

I.32

Extraordinary preference is also given to the compounds of formula I.33, in particular to the compounds of formulae I.33.1 to I.33.180, which differ from the corresponding compounds of formulae I.27.1 to I.27.180 in that $R^c$ is $CH(CH_3)C_2H_5$.

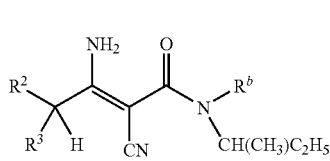

I.33

Extraordinary preference is also given to the compounds of formula I.34, in particular to the compounds of formulae I.34.1 to I.34.180, which differ from the corresponding compounds of formulae I.27.1 to I.27.180 in that $R^c$ is $tC_4H_9$.

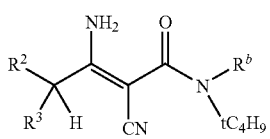

I.34

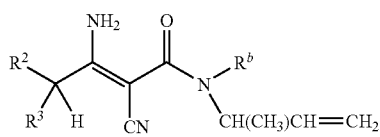

Extraordinary preference is also given to the compounds of formula I.35, in particular to the compounds of formulae I.35.1 to I.35.180, which differ from the corresponding compounds of formulae I.27.1 to I.27.180 in that $R^c$ is $CH(CH_3)CH=CH_2$.

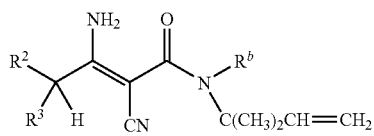

I.35

Extraordinary preference is also given to the compounds of formula I.36, in particular to the compounds of formulae I.36.1 to I.36.180, which differ from the corresponding compounds of formulae I.27.1 to I.27.180 in that $R^c$ is $C(CH_3)CH=CH_2$.

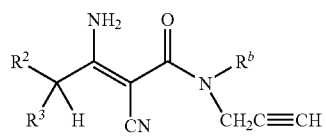

I.36

Extraordinary preference is also given to the compounds of formula I.37, in particular to the compounds of formulae I.37.1 to I.37.180, which differ from the corresponding compounds of formulae I.27.1 to I.27.180 in that $R^c$ is $CH_2C\equiv CH$.

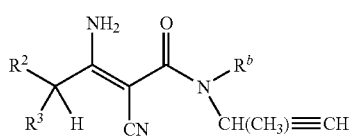

I.37

Extraordinary preference is also given to the compounds of formula I.38, in particular to the compounds of formulae I.38.1 to I.38.180, which differ from the corresponding compounds of formulae I.27.1 to I.27.180 in that $R^c$ is $CH(CH_3)C\equiv CH$.

I.38

Extraordinary preference is also given to the compounds of formula I.39, in particular to the compounds of formulae I.39.1 to I.39.180, which differ from the corresponding compounds of formulae I.27.1 to I.27.180 in that $R^c$ is 3-tetrahydrofuranyl.

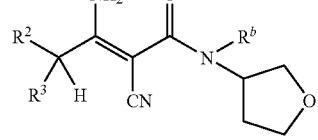

I.39

Extraordinary preference is also given to the compounds of formula I.40, in particular to the compounds of formulae I.40.1 to I.40.180, which differ from the corresponding compounds of formulae I.27.1 to I.27.180 in that $R^c$ is 4-tetrahydropyranyl.

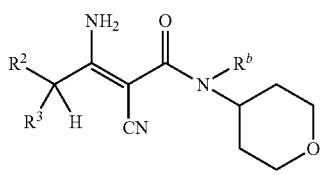

I.40

Extraordinary preference is also given to the compounds of formula I.41 (corresponds to formula I wherein $R^1$ is $NR^bR^c$ wherein $R^b$ and $R^c$ from a 1,4-butandiyl-chain and $R^4$ is hydrogen), in particular to the compounds of formulae I.41.1 to I.41.36 of table 3, where the definitions of the variables $R^1$ to $R^4$ are of particular importance for the compounds according to the invention not only in combination with one another but in each case on their own.

TABLE 3

I.41

| No. | $R^2$ | $R^3$ |
|---|---|---|
| I.41.1 | $C_2H_5$ | $C_2H_5$ |
| I.41.2 | $C_2H_5$ | $nC_3H_7$ |
| I.41.3 | $C_2H_5$ | $iC_3H_7$ |
| I.41.4 | $C_2H_5$ | $nC_4H_9$ |
| I.41.5 | $C_2H_5$ | $CH_2CH(CH_3)_2$ |
| I.41.6 | $C_2H_5$ | $CH(CH_3)C_2H_5$ |
| I.41.7 | $C_2H_5$ | $CH_2CH=CH_2$ |
| I.41.8 | $C_2H_5$ | $CH_2C\equiv CH$ |
| I.41.9 | $nC_3H_7$ | $nC_3H_7$ |
| I.41.10 | $nC_3H_7$ | $iC_3H_7$ |
| I.41.11 | $nC_3H_7$ | $nC_4H_9$ |
| I.41.12 | $nC_3H_7$ | $CH_2CH(CH_3)_2$ |
| I.41.13 | $nC_3H_7$ | $CH(CH_3)C_2H_5$ |
| I.41.14 | $nC_3H_7$ | $CH_2CH=CH_2$ |
| I.41.15 | $nC_3H_7$ | $CH_2C\equiv CH$ |
| I.41.16 | $iC_3H_7$ | $iC_3H_7$ |
| I.41.17 | $iC_3H_7$ | $nC_4H_9$ |
| I.41.18 | $iC_3H_7$ | $CH_2CH(CH_3)_2$ |
| I.41.19 | $iC_3H_7$ | $CH(CH_3)C_2H_5$ |
| I.41.20 | $iC_3H_7$ | $CH_2CH=CH_2$ |
| I.41.21 | $iC_3H_7$ | $CH_2C\equiv CH$ |
| I.41.22 | $nC_4H_9$ | $nC_4H_9$ |
| I.41.23 | $nC_4H_9$ | $CH_2CH(CH_3)_2$ |

TABLE 3-continued

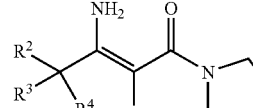

I.41

| No. | $R^2$ | $R^3$ |
|---|---|---|
| I.41.24 | $nC_4H_9$ | $CH(CH_3)C_2H_5$ |
| I.41.25 | $nC_4H_9$ | $CH_2CH=CH_2$ |
| I.41.26 | $nC_4H_9$ | $CH_2C\equiv CH$ |
| I.41.27 | $CH_2CH(CH_3)_2$ | $CH_2CH(CH_3)_2$ |
| I.41.28 | $CH_2CH(CH_3)_2$ | $CH(CH_3)C_2H_5$ |
| I.41.29 | $CH_2CH(CH_3)_2$ | $CH_2CH=CH_2$ |
| I.41.30 | $CH_2CH(CH_3)_2$ | $CH_2C\equiv CH$ |
| I.41.31 | $CH(CH_3)C_2H_5$ | $CH(CH_3)C_2H_5$ |
| I.41.32 | $CH(CH_3)C_2H_5$ | $CH_2CH=CH_2$ |
| I.41.33 | $CH(CH_3)C_2H_5$ | $CH_2C\equiv CH$ |
| I.41.34 | $CH_2CH=CH_2$ | $CH_2CH=CH_2$ |
| I.41.35 | $CH_2CH=CH_2$ | $CH_2C\equiv CH$ |
| I.41.36 | $CH_2C\equiv CH$ | $CH_2C\equiv CH$ |

Extraordinary preference is also given to the compounds of formula I.42, in particular to the compounds of formulae I.42.1 to I.42.36, which differ from the corresponding compounds of formulae I.41.1 to I.41.36 in that $R^1$ is $NR^bR^c$ wherein $R^b$ and $R^c$ form a 1,5 pentanediyl-chain.

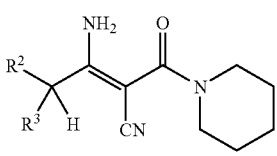

I.42

Extraordinary preference is also given to the compounds of formula I.43, in particular to the compounds of formulae I.43.1 to I.43.36, which differ from the corresponding compounds of formulae I.41.1 to I.41.36 in that $R^1$ is $NR^bR^c$ wherein $R^b$ and $R^c$ form a 1,6-hexanediyl-chain.

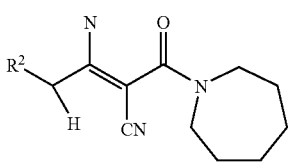

I.43

Extraordinary preference is also given to the compounds of formula I.44, in particular to the compounds of formulae I.44.1 to I.44.36, which differ from the corresponding compounds of formulae I.41.1 to I.41.36 in that $R^1$ is $SR^d$ wherein $R^d$ is $CH_3$.

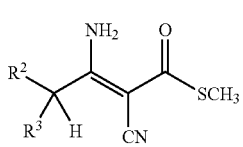

I.44

Extraordinary preference is also given to the compounds of formula I.45, in particular to the compounds of formulae I.45.1 to I.45.36, which differ from the corresponding compounds of formulae I.41.1 to I.41.36 in that $R^1$ is $SR^d$ wherein $R^d$ is $C_2H_5$.

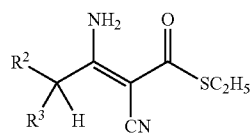

I.45

Extraordinary preference is also given to the compounds of formula I.46, in particular to the compounds of formulae I.46.1 to I.46.36, which differ from the corresponding compounds of formulae I.41.1 to I.41.36 in that $R^1$ is $SR^d$ wherein $R^d$ is $nC_3H_7$.

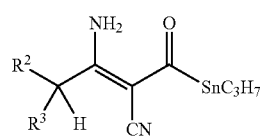

I.46

Extraordinary preference is also given to the compounds of formula I.47, in particular to the compounds of formulae I.47.1 to I.47.36, which differ from the corresponding compounds of formulae I.41.1 to I.41.36 in that $R^1$ is $SR^d$ wherein $R^d$ is $iC_3H_7$.

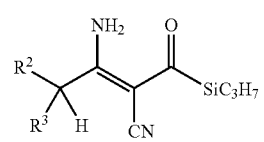

I.47

Extraordinary preference is also given to the compounds of formula I.48, in particular to the compounds of formulae I.48.1 to I.48.36, which differ from the corresponding compounds of formulae I.41.1 to I.41.36 in that $R^1$ is $SR^d$ wherein $R^d$ is $CH_2CH(CH_3)$.

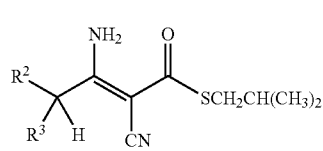

I.48

Extraordinary preference is also given to the compounds of formula I.49, in particular to the compounds of formulae I.49.1 to I.49.36, which differ from the corresponding compounds of formulae I.41.1 to I.41.36 in that $R^1$ is $SR^d$ wherein $R^d$ is $CH(CH_3)C_2H_5$.

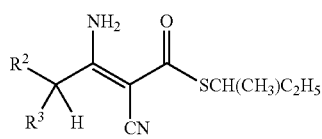
I.49

Extraordinary preference is also given to the compounds of formula I.50, in particular to the compounds of formulae I.50.1 to I.50.36, which differ from the corresponding compounds of formulae I.41.1 to I.41.36 in that $R^1$ is $SR^d$ wherein $R^d$ is $tC_4H_9$.

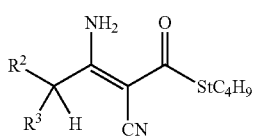
I.50

Extraordinary preference is also given to the compounds of formula I.51, in particular to the compounds of formulae I.51.1 to I.51.36, which differ from the corresponding compounds of formulae I.41.1 to I.41.36 in that $R^1$ is $SR^d$ wherein $R^d$ is $CH(CH_3)CH=CH_2$.

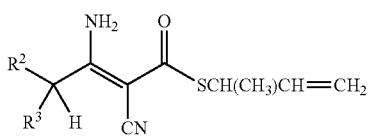
I.51

Extraordinary preference is also given to the compounds of formula I.52, in particular to the compounds of formulae I.52.1 to I.52.36, which differ from the corresponding compounds of formulae I.41.1 to I.41.36 in that $R^1$ is $SR^d$ wherein $R^d$ is $C(CH_3)_2CH=CH_2$.

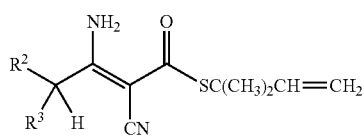
I.52

Extraordinary preference is also given to the compounds of formula I.53, in particular to the compounds of formulae I.53.1 to I.53.36, which differ from the corresponding compounds of formulae I.41.1 to I.41.36 in that $R^1$ is $SR^d$ wherein $R^d$ is $CH_2C\equiv CH$.

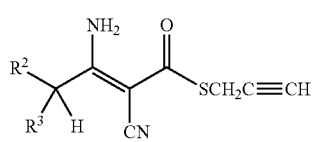
I.53

Extraordinary preference is also given to the compounds of formula I.54, in particular to the compounds of formulae I.54.1 to I.54.36, which differ from the corresponding compounds of formulae I.41.1 to I.41.36 in that $R^1$ is $SR^d$ wherein $R^d$ is $CH(CH_3)C\equiv CH$.

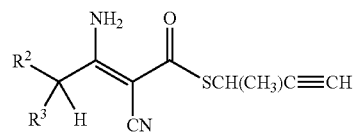
I.54

Extraordinary preference is also given to the compounds of formula I.55, in particular to the compounds of formulae I.55.1 to I.55.36, which differ from the corresponding compounds of formulae I.41.1 to I.41.36 in that $R^1$ is $SR^d$ wherein $R^d$ is 3-tetrahydrofuranyl.

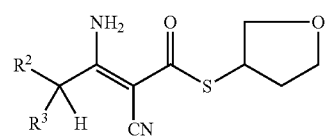
I.55

In the synthesis of the α-cyanoacrylates, the starting materials or products in question are usually present in an (E):(Z) ratio of from 95:5 to 5:95. It is possible to separate the isomers, for example by chromatographic purification, and to continue the reactions with the pure isomer in question.

The α-cyanoacrylates of formula I can be prepared by various routes, for example by the following processes:

Process A

Cyanoacetic derivatives of formula IV are reacted with carbonyl chlorides of the formula V to give enols of the formula III. Following conversion of the enol OH-group, the corresponding enol ether of the formula II is obtained, which is then converted with ammonia into the desired α-cyanoacrylate:

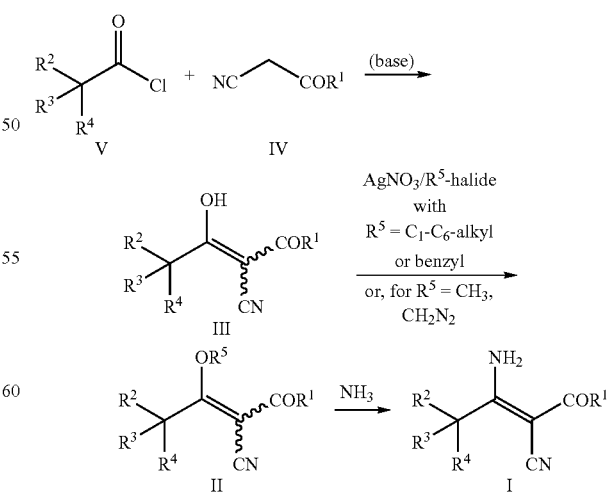

where $R^5$ is for example methyl, ethyl or benzyl

Preferably compounds of formula I wherein $R^1$ is $OR^a$ are prepared according to this process. However compounds of formula I wherein $R^1$ is $NR^bR^c$ or $SR^d$ can be prepared analogous.

The conversion of the cyanoacetic ester of formula IV with carbonyl chlorides of formula V into enols of the formula III is usually carried out at temperatures of from 0° C. to 15° C., preferably at 0° C., in an inert organic solvent, if appropriate in the presence of a base [cf. Haller et al., C. R. Acad. Sc. 15 (1887), 115; Dieckmann et al., Chem. Ber. 37 (1904), 3384; Michael et al., Chem. Ber. 38 (1905), 50; Guinchant, Ann. Chim. 9 (1918), 49].

Suitable solvents are aliphatic hydrocarbons such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, particularly preferably methylene chloride, tert-butyl methyl ether, diethyl ether, tetrahydrofuran and acetonitrile.

It is also possible to use mixtures of solvents mentioned.

Suitable bases are, in general, inorganic compounds, such as alkali metal and alkaline earth metal alkoxides, such as sodium methoxide, sodium ethoxide, potassium ethoxide, potassium tert-butoxide, potassium tert-pentoxide and dimethoxymagnesium, and furthermore organic bases, for example tertiary amines, such as trimethylamine, triethylamine, diisoproylethylamine and N-methylpiperidine, pyridine, substituted pyridines such as collidine, lutidine, N-methylmorpholine and 4-dimethylaminopyridine, and also bicyclic amines. Particular preference is given to sodium ethoxide and triethylamine.

The bases are generally employed in excess or they can, if appropriate, be used as solvent.

IV is generally employed in excess, based on V.

The reaction mixtures are worked up in a customary manner, for example by mixing with water, separation of the phases and, if appropriate, chromatographic purification of the crude products. Some of the intermediates and end products are obtained in the form of viscous oils which can be purified or freed from volatile components under reduced pressure and at moderately elevated temperature. If the intermediates and end products are obtained as solid, purification can also be carried out by recrystallization or digestion.

The enol ethers of formula II can be obtained by alkylation of the silver salt of the enol of the formula III.

The reaction of the enol of formula III with silver nitrate is usually carried out in water at 25° C. [cf. Haller, Comp. Rend. 130 (1900), 1221].

The reaction of the silver salt of the enol of formula III with an alkylating agent is usually carried out at from 25° C. to 80° C. in an inert organic solvent [cf. Haller, Comp. Rend. 130 (1900), 1221].

Suitable solvents are halogenated hydrocarbons, such as methylene chloride, chloroform and chlorobenzene, ethers, such as diethyl ether, diisopropyl ether, tert-butyl methyl ether, dioxane, anisole and tetrahydrofuran, and nitriles, such as acetonitrile and propionitrile, particularly preferably acetonitrile.

It is also possible to use mixtures of the solvents mentioned.

Suitable alkylating agents $R^5$-halides are alkyl halides with $R^5$=$C_1$-$C_6$-alkyl, such as, for example, methyl or ethyl iodide and also methyl or ethyl bromide. For converting III into II, it is furthermore also possible to use benzyl halides with $R^5$=benzyl, such as, for example, benzyl chloride or benzyl bromide.

In general, the alkylating agent is employed in an excess, based on the silver salt of the acrylocyanoacetic ester of formula III.

Work-up can be carried out in a manner known per se to afford the product.

For obtaining the enol ether of formula II wherein $R^5$ is methyl, the enol of formula III can also be reacted with diazomethane. This reaction is usually carried out at from 0° C. to 20° C. in an inert organic solvent [cf. Arndt et al., Liebigs Ann. 521 (1936), 108].

Suitable solvents are ethers, such as diethyl ether, diisopropyl ether, tert-butyl methyl ether, dioxane, anisole and tetrahydrofuran, particularly preferably diethyl ether.

It is also possible to use mixtures of the solvents mentioned.

The starting materials are generally reacted with each other in equimolar amounts. It may be advantageous to employ an excess of diazomethane, based on the enol of formula III.

Instead of diazomethane, it is also possible to use, for example, trimethylsilyldiazomethane.

Work-up can be carried out in a manner known per se to afford the product.

The enol ethers of formula II can also be obtained by reacting, for example, orthoesters of formula VII, where $R^5$ is a $C_1$-$C_4$-alkyl radical, such as, for example, methyl or ethyl, with the appropriate cyanoacetic esters of formula IV:

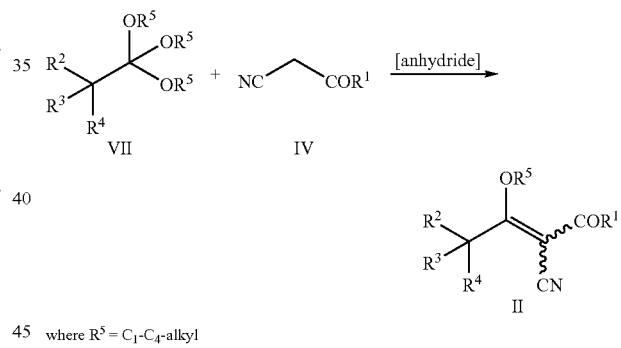

where $R^5$ = $C_1$-$C_4$-alkyl

This reaction is usually carried out at from 100° C. to 150° C., preferably at from 110° C. to 130° C., in the presence of a carboxylic anhydride [cf. Xia et al., J. Med. Chem. 40 (1997), 4372].

Suitable solvents are carboxylic anhydrides, such as acetic anydride or propionic anhydride.

In general, an excess of VII is employed, based on IV.

The orthoesters required for preparing the compounds VI are known from the literature [cf. Houben-Weyl, 1965, Vol. 6/3, 300 f.], or they can be prepared in accordance with the literature cited and/or are commercially available.

The reaction of the enol ethers of formula II with ammonia or an ammonia-containing solution is usually carried out at from 0° C. to 20° C., preferably from 0° C. to 10° C., in an inert organic solvent [cf. Haller, Comp. Rend. 130 (1900), 1221].

Suitable solvents are ethers, such as diethyl ether, diisopropyl ether, tert-butyl methyl ether, dioxane, anisole and tetrahydrofuran, nitriles, such as acetonitrile and propionitrile, alkohols, such as methanol, ethanol, n-propanol, isopropanol, n-butanol and tert-butanol, particularly preferably acetonitrile.

It is also possible to use mixtures of the solvents mentioned.

In general, an excess of ammonia is employed, based on II.

Work-up can be carried out in a manner known per se to afford the product.

The starting materials required for preparing the compounds I are known from the literature [Dahn et al., Helv. Chim. Acta 42 (1959), 1214; Bowie, Tetrahedron 23 (1967), 305], or they can be prepared in accordance with the literature cited and/or are commercially available.

Process B

Enols of formula III are reacted with acid chlorides $R^6COCl$ to give enol derivates of the formula VI, which are then reacted with ammonia to give the desired α-cyanoacrylates:

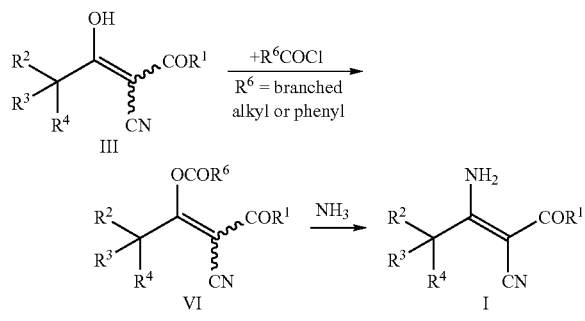

Preferably compounds of formula I wherein $R^1$ is $OR^a$ are prepared according to this process. However compounds of formula I wherein $R^1$ is $NR^bR^c$ or $SR^d$ can be prepared analogous.

$R^6COCl$ are customary acid chlorides which are commercially available, such as, for example, acetic acid chlorid, isobutyryl chloride or pivaloyl chloride. $R^6$ is $C_1$-$C_6$-alkyl (such as, for example, methyl, ethyl, isopropyl or tert.-butyl), phenyl or benzyl. Preference is given to acid chlorides having sterically demanding radicals $R^6$, such as, for example, branched $C_3$-$C_6$-alkyl or phenyl.

The conversion of the enols of formula III with acid chlorides into enol esters of formula VI is usually carried out at from 0° C. to 35° C., preferably at 25° C., in an inert organic solvent in the presence of a base [cf. Haller, Comp. Rend. 130 (1900), 1221; Schmitt, Bull. Soc. Chim. France 31 (1904), 325].

Suitable solvents are aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, particularly preferably acetonitrile.

It is also possible to use mixtures of the solvents mentioned.

Optionally the reaction can be carried out in the presence of a base.

Suitable bases are, in general, inorganic compounds, such as alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal and alkaline earth metal alkoxides, such as sodium methoxide, sodium ethoxide, potassium ethoxide, potassium tert-butoxide, potassium tert-pentoxide and dimethoxymagnesium, furthermore organic bases, for example tertiary amines, such as trimethylamine, triethylamine, diisopropylethylamine, N-methyl-piperidine, pyridine, substituted pyridines, such as collidine, lutidine and 4-dimethylaminopyridine, and also bicyclic amines. Particular preference is given to alkoxides.

The bases are generally employed in equimolar amounts.

The starting materials are generally reacted with one another in equimolar amounts. It may be advantageous to employ an excess of acid chloride, based on III.

Work-up can be carried out in a manner known per se to afford the product.

The enols of the formula III required for preparing the compounds VI can be prepared according to Process A.

The reaction of the enol esters of the formula VI with ammonia or an ammonia-containing solution is carried out under the same conditions as described in Process A.

Process C

Reaction of the enols of formula III with $POCl_3$ and subsequent reaction of the crude reaction mixture with ammonia likewise gives α-cyanoacrylates of formula I:

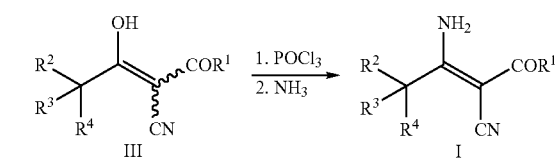

Preferably compounds of formula I wherein $R^1$ is $OR^a$ are prepared according to this process. However compounds of formula I wherein $R^1$ is $NR^bR^c$ or $SR^d$ can be prepared analogous.

The reaction with $POCl_3$ is usually carried out at from 0° C. to 100° C., preferably at 0 to 50° C., particular preferably 0 to 25° C., most preferably at 0° C., in an inert organic solvent in the presence of a base [cf. DE 1 935 630].

Suitable solvents for the reaction with $POCl_3$ are aromatic hydrocarbons, such as toluene, o-, m- and p-xylene, halogenated hydrocarbons, such as methylene chloride, chloroform and chlorobenzene, particularly preferably methylene chloride, chloroform and toluene.

It is also possible to use mixtures of the solvents mentioned.

Suitable bases are, in general, organic bases, for example tertiary amines, such as trimethylamine, triethylamine, diisopropylethylamine, N-methylpiperidine, pyridine, substituted pyridines, such as collidine, lutidine and 4-dimethylaminopyridine, and also bicyclic amines. Particular preference is given to triethylamine.

The bases are generally employed in excess.

Following gentle concentration of the reaction mixture, the subsequent reaction, with ammonia, of the enol phosphate formed in the reaction is preferably carried out in nitriles, such as acetonitrile or propionitrile.

In general, an excess of $POCl_3$ and $NH_3$ is used, based on III.

Process D

The reaction of imido esters of formula VIII, previously released, for example, from the corresponding hydrochlorides using a base, with cyanoacetic derivatives of formula IV also gives α-cyanoacrylates of formula I:

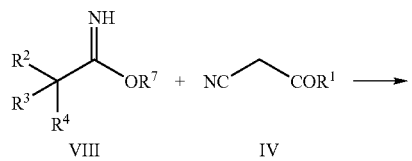

where $R^7 = C_1\text{-}C_6\text{-alkyl}$

Preferably compounds of formula I wherein $R^1$ is $OR^a$ are prepared according to this process. However compounds of formula I wherein $R^1$ is $NR^bR^c$ or $SR^d$ can be prepared analogous.

$R^7$ is a $C_1\text{-}C_6$-alkyl radical such as, for example, methyl or ethyl.

The imido esters are usually released from their salts using bases, such as potassium carbonate [cf. Houben-Weyl 1952, Vol. 8, 697].

The reaction with cyanoacrylates of formula IV is usually carried out at from 50° C. to 100° C., preferably at from 80° C. to 90° C., in an organic solvent [cf. Kenner et al., J. Chem. Soc. 1943, 388].

Suitable solvents are ethers, such as dioxane, anisole and tetrahydrofuran, nitriles, such as acetonitrile and propionitrile, alcohols, such as methanol, ethanol, n-propanol, isopropanol, n-butanol and tert-butanol, particularly preferably ethanol.

It is also possible to use mixtures of other solvents mentioned.

The starting materials are generally reacted with one another in equimolar amounts. It may be advantageous to employ an excess of VIII, based on IV.

The imido ester hydrochlorides required for preparing the compounds I are known from the literature [cf. Pinner, Die Iminoäther und ihre Derivate, [The imino ethers and their derivatives], Berlin 1892] or they can be prepared in accordance with the literature cited, especially from the respective nitriles.

Process E

The reaction of amidines of formula IX, previously released, for example, from the corresponding hydrochlorides using a base, with cyanoacetic derivatives of formula IV also gives α-cyanoacrylates of formula I:

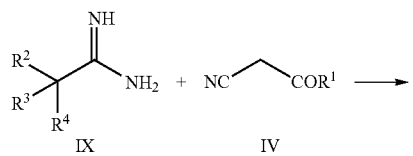

-continued

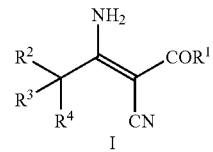

Preferably compounds of formula I wherein $R^1$ is $OR^a$ are prepared according to this process. However compounds of formula I wherein $R^1$ is $NR^bR^c$ or $SR^d$ can be prepared analogous.

The amidines are usually released from their salts using bases, such as, for example, potassium carbonate [cf. Houben-Weyl 1952, Vol. 8, 702].

The reaction with cyanoacrylates of formula IV is usually carried out at from 80° C. to 130° C., preferably at from 90° C. to 100° C., in an inert organic solvent [cf. Hull et al., J. Chem. Soc. 1946, 357].

Suitable solvents are aromatic hydrocarbons, such as toluene, o-, m- and p-xylene, alcohols, such as ethanol, n-propanol, isopropanol, n-butanol and tert-butanol, particularly preferably ethanol.

Suitable bases for releasing the amidines from their salts are, in general, inorganic compounds, such as alkali metal and alkaline earth metal carbonates, such as lithium carbonate, potassium carbonate and calcium carbonate, and also alkali metal and alkaline earth metal alkoxides, such as sodium methoxide, sodium ethoxide, potassium ethoxide, potassium tert-butoxide, potassium tert-pentoxide, and furthermore ammonia. Particular preference is given to potassium carbonate and ammonia.

The starting materials are generally reacted with one another in equimolar amounts. It may be advantageous to employ an excess of IX, based on IV.

The amidine hydrochlorides required for preparing the compounds I are known from the literature [Houben-Weyl; 1952, Vol. 8, 702 f.], or they can be prepared in accordance with the literature cited, especially from the respective nitriles.

Process F

Enaminonitriles of formula X are reacted with phosgene (COCl₂) to give the corresponding acid chloride of formula XI, which is then reacted with a compound of formula XII in the presence of a base to give the α-cyanoacrylates of formula I:

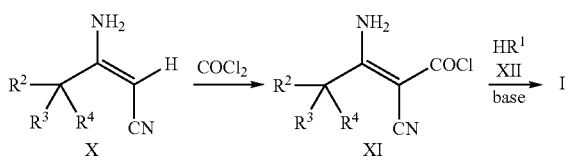

The reaction with phosgene is usually carried out at from 20° C. to 120° C., preferably at from 25° C. to 85° C., in inert organic solvent [cf. Ohoka et al, J. Org. Chem. 38, 1973, 2287].

Suitable solvents are aliphotic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, anisole and tetrahydrofuran, nitriles, such as acacetonitrile and propionitrile, particulary preferably aromatic hydrocarbons such as toluene.

It is also possible to use nitriles of solvents mentioned.

Phosgene is generally employed in excess based on X, preferably are used 4 equivalents of phosgene.

It is also possible to use equivalents of phosgene like diphosgene or triphosgene. Preferred is phosgene.

Works up can be carried out in a manner known per se to afford the product.

The starting materials required for preparing the enaminonitrile of formular X are known from the literature [Fomum et al, J. Chem. Soc. Perkin Trans 1, 1973.1108], or they can be prepared in accerdance with the literature cited.

The reacted of the said chloride of formula XI with a compund of formula XII is usually carried and at temperatures of from 0° C. to 50° C., preferably of from 10° C. to 25° C., in an inert organic solvent in the presence of a base [cf. Ohoka et al., J. Org. Chem. 38, 1973, 2287].

Suitable solvents are aliphatic hydrocarbons such as pentane, hexane, cyclohexane and mixtures of $C_5$-$C_6$-alkanes, aromatic hydrocarbons, such as toluene, o-, m-, and p-xylene, halogenoted hydrocarbons, such as methylene chloride, chloroform and chlorobenzol, ethers, such as diethyl ether, diisopropyl ether, tert.-butyl methyl ether and tetrahydrofuran, nitriles, such as acetonitril and propionitrile, particularly preferably tetrahydrofuran, toluene and tert.-butyl methyl ether.

It is also possible to use mixtures of solvents mentioned.

Suitable bases are, in general, inorganic compounds, such as alkali metal and alkaline earth metal carbonates, such as lithium carbonate, sodium carbonate, potassium carbonate and calcium carbonate; and also alkali metal, hydrogencarbonates, such as sodium hydrogen carbonate; furthermore organic bases, for example tertiary amines, such as trimethylamine, triethylamine, diisopropylethylamine, N-methylpiperidine, pyridine, substituted pyridines such as collidine, lutidine and 4-dimethylaminopyridine, and also bicylic amines. Particular preference is given to trimethylamine.

The bases are generally empolyed in equimolar amounts.

The starting materials are generally reacted with one another in equimolar amounts. It may be advantogeons to empolyan acess of XII based on XI.

α-cyonoacrylates of formula I wherein $R^1$ is $OR^a$ with $R^a$ is hydrogen can for example be prepared by hydrolysis of the respective acid chloride (see Houben-Weyl, 1952, Vol. 8, 425 f) or by hydrolysis of the respective ester (see Houben-Weyl, 1952, Vol. 8, 421 f).

The resulting acid can be transformed by common methods into desired ester derivatives. (Houben-Weyl, 1952, Vol. 8, 516 f, 522 f).

The present invention also provides novel enol ethers of formula II

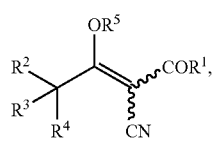

II where $R^1$ to $R^4$ have the meanings mentioned for the compounds of the formula I and $R^5$ is $C_1$-$C_6$-alkyl (such as, for example, methyl or ethyl) or benzyl.

The enol ethers of formula II are present as an (E)/(Z) mixture in a ratio of from 95:5 to 5:95. It is possible to separate the isomers, for example by chromatographic methods.

With respect to the variables, the particularly preferred embodiments of the intermediates correspond to those of radicals $R^1$ to $R^4$ of formula I.

Particular preference is given to the compounds of formula II in wherein $R^1$ is $OR^a$ wherein $R^a$ is branched $C_3$-$C_6$-alkyl;
  particularly preferably 1-methylethyl, 2-methylpropyl or 1,1-dimethylethyl; and
$R^2$ is $C_1$-$C_4$-alkyl;
  particularly preferably methyl, ethyl or n-propyl;
  especially preferably methyl or ethyl;
$R^3$ is $C_2$-$C_4$-alkyl;
  particularly preferably ethyl or n-propyl;
  especially preferably ethyl or n-propyl; and
$R^4$ is hydrogen, fluorine or chlorine;
  particularly preferably hydrogen.

Particular preference is also given to compounds of formula II wherein $R^1$ is $NR^bR^c$ wherein $R^b$ and $R^c$ are independently of each other hydrogen or $C_1$-$C_6$-alkyl;
  preferably hydrogen or $C_1$-$C_4$-alkyl;
  particular preferably hydrogen, ethyl, n-propyl or i-propyl;
$R^2$ is $C_1$-$C_4$-alkyl;
  preferably methyl, ethyl, or n-propyl;
$R^3$ is $C_2$-$C_4$-alkyl;
  preferably ethyl or n-propyl; and
$R^4$ is hydrogen.

Particular preference is also given to compounds of formular II wherein $R^1$ is $SR^d$ wherein $R^d$ is hydrogen or $C_1$-$C_6$-alkyl;
  preferably hydrogen or $C_1$-$C_4$-alkyl;
  particular preferably hydrogen, ethyl, n-propyl or i-propyl;
$R^2$ is $C_1$-$C_4$-alkyl;
  preferably methyl, ethyl, or n-propyl;
$R^3$ is $C_2$-$C_4$-alkyl,
  preferably ethyl or n-propyl; and
$R^4$ is hydrogen.

The present invention also provides novel enol esters of formula VI

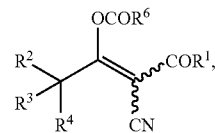

VI where $R^1$ to $R^4$ have the meanings mentioned for the compounds of formula I and $R^6$ is $C_1$-$C_6$-alkyl, (such as, for example, isopropyl or tert-butyl, preferably tert-butyl), phenyl or benzyl.

The enol esters of formula VI are present as an (E)/(Z) mixture in a ratio of from 95:5 to 5:95, usually in a ratio of 50:50. It is possible to separate the isomers, for example by chromatographic methods.

With respect to the variables, the particularly preferred embodiments of the intermediates correspond to those of radicals $R^1$ to $R^4$ in the formula I.

Particular preference is given to the compounds of formula VI in wherein $R^1$ is $OR^a$ wherein
$R^a$ is branched $C_3$-$C_6$-alkyl;
 particularly preferably 1-methylethyl, 2-methylpropyl or 1,1-dimethylethyl; and
$R^2$ is $C_1$-$C_4$-alkyl;
 particularly preferably methyl, ethyl or n-propyl;
 especially preferably methyl or ethyl;
 also especially preferably ethyl or n-propyl;
$R^3$ is $C_2$-$C_4$-alkyl;
 particularly preferably ethyl; and
$R^4$ is hydrogen, fluorine or chlorine;
 particularly preferably hydrogen.

Particular preference is also given to compounds of formular VI wherein $R^1$ is $NR^bR^c$ wherein
$R^b$ and $R^c$ are independently of each other hydrogen or $C_1$-$C_6$-alkyl;
 preferably hydrogen or $C_1$-$C_4$-alkyl;
 particular preferably hydrogen, ethyl, n-propyl or i-propyl;
$R^2$ is $C_1$-$C_4$-alkyl;
 preferably methyl, ethyl, or n-propyl;
$R^3$ is $C_2$-$C_4$-alkyl;
 preferably ethyl or n-propyl; and
$R^4$ is hydrogen.

Particular preference is also given to compounds of formular VI wherein $R^1$ is $SR^d$ wherein
$R^d$ is hydrogen or $C_1$-$C_6$-alkyl;
 preferably hydrogen or $C_1$-$C_4$-alkyl;
 particular preferably hydrogen, ethyl, n-propyl or i-propyl;
$R^2$ is $C_1$-$C_4$-alkyl;
 preferably methyl, ethyl, or n-propyl;
$R^3$ is $C_2$-$C_4$-alkyl;
 preferably ethyl or n-propyl; and
$R^4$ is hydrogen.

EXAMPLE 4.1

Isopropyl (2Z)-3-amino-2-cyano-4-ethyl-2-hexenoate

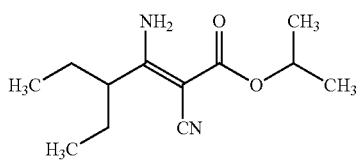

Example 4.1

According to process C:

1. Isopropyl (2Z)-3-hydroxy-2-cyano-4-ethyl-2-hexenoate 22.2 g (0.16 mol) of 2-ethylbutyryl chloride were added to a solution of 21 g (0.16 mol) of isopropyl cyanoacetate in $CH_2Cl_2$, and the reaction mixture was cooled to 0° C. At this temperature, with ice-cooling, 33.5 g (0.33 mol) of triethylamine were added dropwise, and the mixture was then stirred at 25° C. for 2 h. Following subsequent acidic hydrolysis, the organic phase was washed, dried and concentrated. Purification by customary methods gave 24.4 g of the title compound (68% of theory) as a colorless oil (b.p. 70-75° C./1.5 mbar).

2. Isopropyl (2Z)-3-amino-2-cyano-4-ethyl-2-hexenoate 24.4 g (0.11 mol) of isopropyl (2Z)-3-hydroxy-2-cyano-4-ethyl-2-hexenoate were dissolved in $CH_2Cl_2$ and, at 25° C., 33.2 g (0.22 mol) of $POCl_3$ were added. After cooling to 0° C., 43.8 g (0.44 mol) of triethylamine were added dropwise, and the mixture was stirred at 25° C. for 2 h. The solution was then concentrated and the residue was taken up in acetonitrile and cooled to 0° C., and 30 g (0.44 mol) of a 25 percent strength solution of ammonia were added dropwise. After 2 h of stirring, the mixture was concentrated to dryness, the residue was taken up in MTBE (methyl tert-butyl ether) and the organic phase was washed with NaOH and water, dried and concentrated. Purification by customary methods gave 10 g (40% of theory) of the title compound as a colorless solid (m.p. 140° C.).

According to process F:

1. 3-Amino-2-cyano-4-ethyl-2-hexene 13.1 g (94 mmol) of 1-Cyano-3-ethyl-2-oxo-pentane were dissolved in toluene and 15 g (194 mmol) ammonium acetate and 1 ml dry acetic acid were added. The mixture was reflured 2 h and then cooled to room temperature. The mixture was washed, dried and concentrated. Perification by customary methods gove 13. 1 g (100% of theory) of the title compound as a oil.

2. (2Z)-3-Amino-2-cyano-4-ethyl-2-hexenoyl chloride 250 ml toluene were cooled to 0° C. and 40 g (0.4 mol) of phosgene were added. After warming up to 25° C., 13.8 g (0.1 mol) of 3-amino-2-cyano-4-ethyl-2-hexene in toluene were added. The reaction mixture was heated at 70° C. for 4 h, then the unreacted phosgene was removed by blowing out with dry $N_2$. After cooling to 25° C. the product precipitated. Filtration and washing with diethyl ether gave 12 g (60% of theory) of the title compound as a yellow solid (m. p. 102° C.).

3. Isopropyl (2Z)-3-amino-2-cyano-4-ethyl-2-hexenoate 12 g (60 mmol) of (2Z)-3-amino-2-cyano-4-ethyl-2-hexenoyl chloride were dissolved in $CH_2Cl_2$ and 3.6 g (60 mmol) of isopropanole were added. At 20° C. to 25° C. 6.1 g (60 mmol) of triethylamine were added dropwise and the solution was stirred at 25° C. for 4 h. The solution was washed with water, the organic phase was seperated, dried and concentrated. Crystallisation from diisopropyl ether gave 12.4 g of the title compound (92% of theory) as a colorless solid (m.p. 140° C.).

EXAMPLE 4.14

3-Oxetanyl (2Z)-3-amino-2-cyano-4-ethyl-2-hexenoat

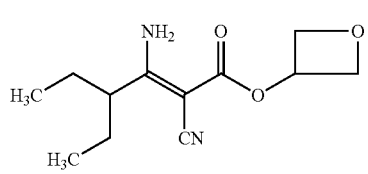

Example 4.14

According to process A:

1. 3-Oxetanyl-cyanoethanoate 23.2 g (0.29 mol) of 3-oxetanol and 3 g (0.025 mol) of dimethylaminopyridine were added to a solution of 25 g (0.29 mol) of cyanoacetic acid in $CH_2Cl_2$. After cooling to 0° C., 66.8 g (0.32 mol) of dicyclohexylcarbodiimide (DCC) in $CH_2Cl_2$ were added dropwise and the reaction micxture was stirred at 25° C. for 2 h. The solid was removed and the solution was concentrated. Purification by customary methods gave 42 g of the title compound (100% of theory) as a colorless oil.

2. 3-Oxetanyl (2Z)-2-cyano-4-ethyl-3-hydroxy-2-hexanoate 42 g (0.29 mol) of 3-oxetanyl-cyanoethanoat were dissolved in $CH_2Cl_2$ and 39 g (0.29 mol) of 2-ethyl-butanoyl cloride were added. The mixture was coold to 0° C. and 29.3 g (0.29 mol) of triethylamine were added. The reaction mixture was stirred at 25° C. for 2 h. Following subsequent acidic hydrolysis the organic phase was washed, dried and concentrated. Purification by customary methods gave 41.5 g of the title compound (60% of theory) as a reddish oil.

3. 3-Oxetanyl (2Z)-3-amino-2-cyano-4-ethyl-2-hexanoat 5 g (21 mmol) of 3-oxetanyl (2Z)-2-cyano-4-ethyl-2-hexanoat were dissolved in acetonitrile and 30 mmol of diazomethane in ether were added at 25° C. After 10 min 50 ml (0.65 mol) of a 25% ammonia solution were added and the reaction mixture was stirred for 1 h. Following subsequent addition of tert.-butyl methyl ether, the organic phase was washed, dried and concentrated. Crystallisation from diisopropyl ether gave 2 g of the title compound (40% of theory) as a colorless solid (m. p. 175° C.).

EXAMPLE 4.42

(2Z)-3-Amino-2-cyano-4-ethyl-2-hexene acid

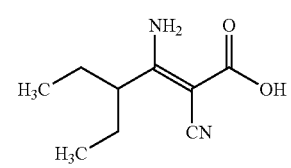

Example 4.42

3 g (15 mmol) of (2Z)-3-amino-2-cyano-4-ethyl-2-hexenoyl chloride dissolved in acetonitrile were added dropwise to a solution of 2.6 g (30 mmol) $NaHCO_3$ in water. The solution was stirred at 25° C. for 30 min, then concentrated to dryness and the residue was taken up in methanol. The precipitate was seperated and the filtrate concencentrated to dryness again. The residue was dissolved in water and saturated $KHSO_4$-solution was added. Filtration of the precipitate gave 2 g of the title compound (73% of theory) as a colorless solid (m. p. 150° C.)

The compounds listed in Table 4 below can be prepared analogously to the above mentioned exemples:

TABLE 4

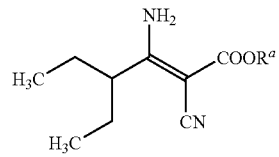

| Example No. | $R^a$ | m.p. [° C.] |
|---|---|---|
| 4.1 | $iC_3H_7$ | 140 |
| 4.2 | $CH(CH_3)CH_2CH_3$ | 162 |
| 4.3 | $CH(CH_2CH_3)_2$ | 178 |
| 4.4 | $C(CH_3)_3$ | 150 |
| 4.5 | $CH_2CH(CH_3)_2$ | 125 |
| 4.6 | $CH_2C(CH_3)_3$ | 160 |
| 4.7 | $C(CH_3)CH(CH_3)_2$ | 114 |
| 4.8 | $CH(CH_3)CH_2CH(CH_3)_2$ | 112 |
| 4.9 | $C(CH3)(C_2H_5)_2$ | 112 |
| 4.10 | cyclopropyl | |
| 4.11 | cyclopentyl | 140 |
| 4.12 | cyclohexyl | 154 |
| 4.13 | cyclopropylmethyl | 125 |
| 4.14 | 3-oxetanyl | 175 |
| 4.15 | 3-thietanyl | |
| 4.16 | $CH(CH_3)CH=CH_2$ | 145 |
| 4.17 | $CH_2C(CH_3)CH_2$ | 78 |
| 4.18 | $C(CH_3)_2CH=CH_2$ | 102 |
| 4.19 | $CH_2C=CH$ | 94 |
| 4.20 | $CH(CH_3)C=CH$ | 134 |
| 4.21 | $C(CH_3)_2C=CH$ | oil |
| 4.22 | $(CH_2)_2CF_3$ | 85 |
| 4.23 | $(CH_2)_2Cl$ | 82 |
| 4.24 | $CH(CH_2Cl)_2$ | 145 |
| 4.25 | $CH_2CF_3$ | 115 |
| 4.26 | $CH_2CCl_3$ | 200 |
| 4.27 | $(CH_2)_2SCH_3$ | 54 |
| 4.28 | $CH(CH_3)CH_2SCH_3$ | |
| 4.29 | $(CH_2)_3Cl$ | 95 |
| 4.30 | $CH(CH_3)CH_2Cl$ | 142 |
| 4.31 | $CH_2CH=C(CH_3)_2$ | 98 |
| 4.32 | $C_6H_5$ | 180 |
| 4.33 | $CH_2C_6H_5$ | 87 |
| 4.34 | $CH(CH_3)C_6H_5$ | 118 |
| 4.35 | $CH(CH_3)CN$ | 68 |
| 4.36 | $CH(CH_3)CO_2CH_3$ | 115-120 |
| 4.37 | $CH(CH_3)CONH_2$ | 180 |
| 4.38 | 3-tetrahydrofuranyl | 105-110 |
| 4.39 | $CH(CH_3)(CF_3)$ | 135 |
| 4.40 | $CH(CF_3)_2$ | 148 |
| 4.41 | $N=C(CH_3)_2$ | 160 |
| 4.42 | H | 165 |
| 4.43 | 2-tetrahydrofuranyl | 180 |

The compounds listed below in table 5 can be prepared analogously to the above mentioned examples:

TABLE 5

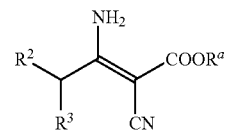

| Example No. | $R^a$ | $R^2$ | $R^3$ | m.p. [° C.] |
|---|---|---|---|---|
| 5.1 | $CH(CH_3)_2$ | $CH_2SCH_3$ | $(CH_2)_4CH_3$ | 96 |
| 5.2 | $CH(CH_3)_2$ | $CH_2OCH_3$ | $CH_2CH_3$ | 80 |
| 5.3 | $CH(CH_3)_2$ | $C_2H_5$ | $nC_3H_7$ | 118-120 |

TABLE 5-continued

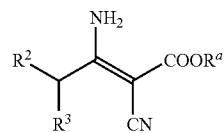

| Example No. | $R^a$ | $R^2$ | $R^3$ | m.p. [° C.] |
|---|---|---|---|---|
| 5.4 | CH(CH₃)₂ | CH₂CH(CH₃)₂ | C₂H₅ | 143-145 |
| 5.5 | CH(CH₃)₂ | C₂H₅ | CH₂CH₂CH(CH₃)₂ | 83-84 |
| 5.6 | CH(CH₃)₂ | nC₃H₇ | nC₃H₇ | 140 |
| 5.7 | CH(CH₃)₂ | CH₂CH=CH₂ | C₂H₅ | 108 |
| 5.8 | CH(CH₃)₂ | CH₂CH=C(CH₃)₂ | C₂H₅ | 103-105 |
| 5.9 | CH(CH₃)₂ | CH₂CH=CH₂ | CH₂CH=CH₂ | 104 |
| 5.10 | CH(CH₃)₂ | CH₂C≡CH | C₂H₅ | 78-80 |
| 5.11 | CH(CH₃)₂ | CH₂CH=CH₂ | CH₂C≡CH | 79 |
| 5.12 | CH(C₂H₅)₂ | CH₃ | CH₃ | 108 |

The compounds listed below in table 6 can be prepared analogous to one of the aforementioned processes:

TABLE 6

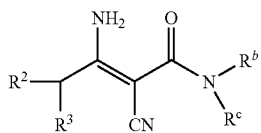

| Example No. | $R^b$ | $R^c$ | $R^2$ | $R^3$ | m.p. [° C.] |
|---|---|---|---|---|---|
| 6.1 | H | H | C₂H₅ | C₂H₅ | 125 |
| 6.2 | H | CH₃ | C₂H₅ | C₂H₅ | 146 |
| 6.3 | H | C₂H₅ | C₂H₅ | C₂H₅ | 104–106 |
| 6.4 | H | nC₃H₇ | C₂H₅ | C₂H₅ | 110 |
| 6.5 | H | CH(CH₃)₂ | C₂H₅ | C₂H₅ | 164 |
| 6.6 | H | CH₂CH(CH₃)₂ | C₂H₅ | C₂H₅ | 139 |
| 6.7 | H | CH(CH₃)C₂H₅ | C₂H₅ | C₂H₅ | |
| 6.8 | H | tC₄H₉ | C₂H₅ | C₂H₅ | 88 |
| 6.9 | H | CH₂CH=CH₂ | C₂H₅ | C₂H₅ | 90 |
| 6.10 | H | C(CH₃)₂CH=CH₂ | C₂H₅ | C₂H₅ | 50 |
| 6.11 | H | CH(CH₃)CH₂OH | C₂H₅ | C₂H₅ | |
| 6.12 | H | CH(CH₃)CH₂OCH₃ | C₂H₅ | C₂H₅ | 100 |
| 6.13 | H | CH(CH₃)CH₂OC₂H₅ | C₂H₅ | C₂H₅ | 47 |
| 6.14 | H | CH(C₂H₅)CH₂OH | C₂H₅ | C₂H₅ | oil |
| 6.15 | H | CH(C₂H₅)CH₂OCH₃ | C₂H₅ | C₂H₅ | 118 |
| 6.16 | H | CH(C₂H₅)CH₂OC₂H₅ | C₂H₅ | C₂H₅ | |
| 6.17 | H | CH(CH₂OH)₂ | C₂H₅ | C₂H₅ | |
| 6.18 | H | CH(CH₃)CH(OCH₃)₂ | C₂H₅ | C₂H₅ | |
| 6.19 | H | 3-tetrahydro-furanyl | C₂H₅ | C₂H₅ | 79 |
| 6.20 | H | (2,2-dimethyl-1,3-dioxan-5-yl) | C₂H₅ | C₂H₅ | |
| 6.21 | CH₃ | CH₃ | C₂H₅ | C₂H₅ | 132 |
| 6.22 | CH₃ | C₂H₅ | C₂H₅ | C₂H₅ | |
| 6.23 | CH₃ | nC₃H₇ | C₂H₅ | C₂H₅ | |
| 6.24 | C₂H₅ | C₂H₅ | C₂H₅ | C₂H₅ | 93 |
| 6.25 | —(CH₂)₄— | | C₂H₅ | C₂H₅ | 73 |
| 6.26 | —(CH₂)₄— | | C₂H₅ | nC₄H₉ | oil |
| 6.27 | —(CH₂)₅— | | C₂H₅ | C₂H₅ | |
| 6.28 | —(CH₂)₆— | | C₂H₅ | C₂H₅ | 125 |
| 6.29 | H | C₂H₅ | C₂H₅ | C₂H₅ | 124 |
| 6.30 | H | CH(C₂H₅)₂ | C₂H₅ | C₂H₅ | 165 |
| 6.31 | H | CH(CH₃)CH(OH)CH₃ | C₂H₅ | C₂H₅ | 154 |
| 6.32 | H | CH(CH₃)CH(OCH₃)₂ | C₂H₅ | C₂H₅ | 71 |
| 6.33 | H | (S)-CH(CH₃)C₂H₅ | C₂H₅ | C₂H₅ | 142 |
| 6.34 | H | (R)-CH(CH₃)C₂H₅ | C₂H₅ | C₂H₅ | 142 |

The compounds listed below in table 7 can be prepared analogous to one of the aforementioned processes:

TABLE 7

| Example No. | $R^d$ | $R^2$ | $R^3$ | m.p. [° C.] |
|---|---|---|---|---|
| 7.1. | C₂H₅ | C₂H₅ | C₂H₅ | |
| 7.2. | nC₃H₇ | C₂H₅ | C₂H₅ | |
| 7.3. | CH(CH₃)₂ | C₂H₅ | C₂H₅ | 115 |

Biological Application

The α-cyanoacrylates of the formula I and their agriculturally useful salts are suitable for use as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method, the compounds in question of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should ensure the finest possible distribution of the active compounds according to the invention.

The herbicidal compositions comprise a herbicidally effective amount of at least one compound of the formula I or an agriculturally useful salt of I and auxiliaries customarily used for formulative crop protection results.

Suitable inert auxiliaries are essentially:

mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds I are employed in a purity of from 90% to 100%, preferably 95% to 100% (according to NMR spectrum).

The formulation examples which follow illustrate the preparation of such products:

I. 20 parts by weight of example 4.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of example 4.13 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of example 5.7 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of example 4.16 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of an active compound of example 4.30 are mixed with 97 parts by weight of finely divided kaolin. This gives a dust which comprises 3% by weight of active compound.

VI. 20 parts by weight of an active compound of example 4.2 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of an active compound of example 5.2 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active compound. This gives a stable emulsion concentrate.

VIII. 1 part by weight of an active compound of example 4.25 is dissolved in a mixture composed of 80 parts by weight of cyclohexanone and 20 parts by weight of Wettol® EM 31 (=nonionic emulsifier based on ethoxylated castor oil from BASF). The mixture can then be diluted with water to the desired concentration of active compound. This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the α-cyanoacrylates of the formula I may be mixed with a large number of representatives of other herbicidal or growth-regulating active compounds and then applied concomitantly. Suitable components for mixtures are, for example, 1,2,4-thiadiazoles, 1,3,4-thiadiazoles, amides, aminophosphoric acid and its derivatives, aminotriazoles, anilides, aryl/hetaryl-oxyalkanoic acids and their derivatives, benzoic acid and its derivatives, benzothiadiazinones, 2-(hetaroyl/aroyl)-1,3-cyclohexanediones, hetaryl aryl ketones, benzyl-isoxazolidinones, meta-CF$_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the α-cyanoacrylates of the formula I was demonstrated by the following greenhouse experiment:

The cultivation containers used were plastic flowerpots containing lomy sand with approximately 3.0% of humus as the substrate. The seeds of the test plants were sown separately for each species.

For the pre-emergence treatment, directly after sowing the active compounds, which had been suspended or emulsified in water, were applied by means of finely distributing nozzles. The containers were irrigated gently to promote germination and growth and subsequently covered with transparent plastic hoods until the plant had rooted. This cover caused uniform germination of the test plants, unless this was adversely affected by reactive compounds. The application rate for a pre-emergence treatment was 0.5 or 1.0 kg of a.s. (active substance)/ha.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.5 or 1.0 kg of a.s. (active substance)/ha.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were of the following species:

| Scientific name | Common name |
| --- | --- |
| Amaranthus retroflexus | pig weed |
| Digitaria sanguinalis | hairy fingergrass |
| Pharbitis purpurea | common morningglory |
| Setaria faberii | giant foxtail |

The effect of example 4.1, applied by the pre-emergence method at application rates of 1.0 kg/ha, on the harmful plants *Amaranthus retroflexus* and *Setaria faberii* was very good.

At an application rate of 1.0 kg/ha, example 4.1 has shown very good post-emergence activity against the undesirable plants *Pharbitis purpurea* and *Setaria faberii*.

At an application rate of 1.0 kg/ha at pre-emergence conditions the effect on harmful plants *Digitaria sanguinalis* and *Sateria faberii* of examples 4.5, 4.13, 4.16, 4.20, 4.30 and 5.7 was very good.

The effect of example 4.4, 4.6, 4.11, 4.14, 4.23, 4.25, 5.2, 5.3, 5.10 and 6.3 applied under the some conditions on the harmful plant *Setaria faberii* was very good.

Examples 4.7, 4.29 and 4.35 has shown a good effect under the some conditions against *Setaria faberii*.

At an application rate of 0.5 kg/ha at pre-emergence conditions the effect on harmful plants *Digitaria sanguinalis* and *Sateria faberii* of examples 4.2, 4.19, and 4.22 was very good.

The effect of example 4.17 applied under the some conditions on the harmful plant *Digitaria sanguinalis* was very good and applied on *Setaria faberii* was very good.

At an application rate of 1.0 kg/ha at post-emergence conditions the effect of examples 4.4, 4.5, 4.6, 4.11, 4.20, 4.23, 4.29, 5.2, 5.6, 5.7, 5.9, 5.11, 6.3 and 7.3 was very good against undesirable plant *Pharbitis purpurea*. Example 4.7 has shown under the some conditions a good activity against *Pharbitis purpurea*. Example 4.2 has shown a very good post-emergence actirity against *Pharbitis purpurea* at an application rate of 0.5 kg/ha.

We claim:

1. An α-cyanoacrylate of formula I

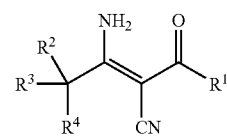

where:
R$^1$ is OR$^a$ wherein R$^a$ is hydrogen, C$_1$-C$_6$-alkyl which is partially or fully halogenated and/or is substituted by a substituent selected from the group consisting of: hydroxy, cyano, C$_3$-C$_6$-cycloalkyl, three- to six-membered heterocyclyl, C$_1$-C$_6$-haloalkoxy, C$_1$-C$_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, ($C_1$-$C_4$)alkoxycarbonyl, aminocarbonyl, ($C_1$-$C_6$)alkylaminocarbonyl and di($C_1$-$C_6$) alkylaminocarbonyl;
  is branched $C_3$-$C_6$-alkyl, branched $C_4$-$C_6$-alkenyl, $C_3$-$C_6$-alkynyl, $C_3$-$C_6$-cycloalkyl, four- to six-membered heterocyclyl, aryl, phenyl($C_1$-$C_4$)alkyl or ($C_1$-$C_6$)alkylimino;
is $NR^bR^c$ wherein $R^b$ is hydrogen, $C_1$-$C_6$-alkyl which may be partially or fully halogenated and/or may be substituted by a substituent selected from the group consisting of: hydroxy, cyano, $C_1$-$C_6$-alkoxy, $C_1$-$C_6$-haloalkoxy, $C_1$-$C_6$-alkylthio, $C_1$-$C_6$-halogenalkylthio, $C_1$-$C_6$-alkylsulfinyl, $C_1$-$C_6$-halogenalkylsulfinyl, $C_1$-$C_6$-alkylsulfonyl and $C_1$-$C_6$-halogenalkylsulfonyl;
  is $C_2$-$C_6$-alkenyl, $C_2$-$C_6$-alkynyl;
  $R^c$ is hydrogen, $C_1$-$C_6$-alkyl which may be partially or fully halogenated and/or may be substituted by a substituent selected from the group consisting of: hydroxy, cyano, $C_3$-$C_6$-cycloalkyl, three- to six-membered heterocyclyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, ($C_1$-$C_4$)alkoxycarbonyl, aminocarbonyl, ($C_1$-$C_6$)alkylaminocarbonyl and di($C_1$-$C_6$)alkylaminocarbonyl;
  is $C_3$-$C_6$-alkenyl, $C_3$-$C_6$-alkynyl, $C_3$-$C_6$-cycloalkyl, four- to six-membered heterocyclyl, aryl, phenyl($C_1$-$C_4$-)alkyl or ($C_1$-$C_6$)alkylimino;
  or $R^b$ and $R^c$ together from a 1,4-butanediyl-, 1,5-pentanediyl- or 1,6-hexanediyl-chain, wherein each of the chains may be substituted by one or more $C_1$-$C_6$-alkyl groups; or
is $SR^d$ wherein $R^d$ has the same meaning as $R^c$;
$R^2$ is $C_1$-$C_6$-alkyl which may be partially or fully halogenated and/or may be substituted by a substituent selected from the group consisting of: cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl;
  is $C_2$-$C_6$-alkenyl or $C_2$-$C_6$-alkynyl;
$R^3$ is $C_2$-$C_6$-alkyl or $C_1$-$C_6$-alkyl which is partially or fully halogenated and/or is substituted by a substituent selected from the group consisting of: cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl;
  is $C_2$-$C_6$-alkenyl or $C_2$-$C_6$-alkynyl;
$R^4$ is hydrogen, halogen, cyano or $C_1$-$C_6$-alkyl,
or an agriculturally useful salt thereof.

2. An α-cyanoacrylate of formula I as claimed in claim 1 wherein $R^1$ is $OR^a$.

3. An α-cyanoacrylate of formula I as claimed in claim 1 wherein $R^1$ is $OR^a$ and $R^a$ is branched $C_3$-$C_6$-alkyl.

4. An α-cyanoacrylate of formula I as claimed in claim 1 wherein $R^1$ is $OR^a$ and $R^2$ is $C_1$-$C_6$-alkyl.

5. An α-cyanoacrylate of formula I as claimed in claim 1 wherein $R^1$ is $OR^a$ and $R^3$ is $C_2$-$C_6$-alkyl.

6. An α-cyanoacrylate of formula I as claimed in claim 1 wherein $R^1$ is $OR^a$ and $R^4$ is hydrogen.

7. An α-cyanoacrylate of formula I as claimed in claim 1 wherein
$R^1$ is $OR^a$, wherein $R^a$ is branched $C_3$-$C_6$-alkyl;
$R^2$ is $C_1$-$C_4$-alkyl;
$R^3$ is $C_2$-$C_4$-alkyl; and
$R^4$ is hydrogen.

8. A process for preparing α-cyanoacrylates of formula I as claimed in claim 1, which comprises reacting an enol ether of formula II

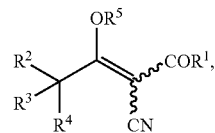

where $R^1$, $R^2$, $R^3$ and $R^4$ are as defined under claim 1 and $R^5$ is $C_1$-$C_6$-alkyl or benzyl with ammonia.

9. A process for preparing α-cyanoacrylates of formula I as claimed in claim 1, which comprises reacting an enol ester of formula VI

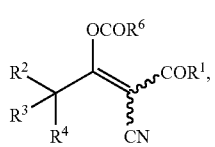

where $R^1$, $R^2$, $R^3$ and $R^4$ are as defined under claim 1 and $R^6$ is $C_1$-$C_6$-alkyl, phenyl or benzyl with ammonia.

10. A process for preparing α-cyanoacrylates of formula I as claimed in claim 1, which comprises reacting an imido ester of formula VIII

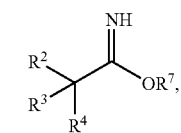

where $R^2$, $R^3$ and $R^4$ are as defined under claim 1 and $R^7$ is an $C_1$-$C_6$-alkyl radical with a compound of formula IV

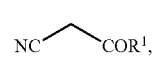

where $R^1$ is as defined under claim 1.

11. A process for preparing α-cyanoacrylates of formula I as claimed in claim 1, which comprises reacting an amidine of formula IX

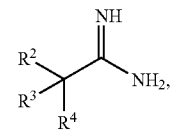

where $R^2$, $R^3$ and $R^4$ are as defined under claim 1 with a compound of formula IV,

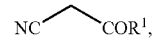

where $R^1$ is as defined under claim 1.

12. A process for preparing α-cyanoacrylates of formula I as claimed in claim 1, which comprises reacting an enaminonitril of formula X

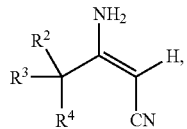

X where $R^2$, $R^3$ and $R^4$ are as defined under claim 1, with phosgene, diphosgene or triphosgene, and subsequent reacting with a compound of formula $HR^1$, optionally in presence of a base, where $R^1$ is as defined under claim 1.

13. A composition, comprising a herbicidally effective amount of at least one α-cyanoacrylate of formula I or an agriculturally useful salt of I as claimed in claim 1 and auxiliaries customary for formulating crop protection agents.

14. A process for preparing compositions as claimed in claim 13, which comprises mixing a herbicidally effective amount of at least one α-cyanoacrylate of formula I or an agriculturally useful salt of I and auxiliaries customary for formulating crop protection agents.

15. A method for controlling undesirable vegetation, which comprises allowing a herbicidally effective amount of at least one α-cyanoacrylate of formula I as claimed in claim 1 or an agriculturally useful salt of I to act on plants, their habitat and/or seeds.

* * * * *